(12) United States Patent
Townley et al.

(10) Patent No.: US 10,806,921 B2
(45) Date of Patent: *Oct. 20, 2020

(54) DEVICES, SYSTEMS, AND METHODS FOR SPECIALIZING, MONITORING, AND/OR EVALUATING THERAPEUTIC NASAL NEUROMODULATION

(71) Applicant: National University of Ireland, Galway, Galway (IE)

(72) Inventors: David Townley, County Clare (IE); Brian Shields, Galway (IE); Ivan Keogh, Galway (IE); Peter Dockery, Galway (IE); Ian Stephen O'Brien, Galway (IE); Martin O'Halloran, Galway (IE); Emily Elizabeth Porter, Galway (IE); Marggie Jones, Galway (IE)

(73) Assignee: National University of Ireland, Galway, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 16/696,826

(22) Filed: Nov. 26, 2019

(65) Prior Publication Data

US 2020/0101283 A1 Apr. 2, 2020

Related U.S. Application Data

(63) Continuation of application No. 16/692,746, filed on Nov. 22, 2019, which is a continuation of application No. 15/811,449, filed on Nov. 13, 2017.
(Continued)

(51) Int. Cl.
*A61B 18/04* (2006.01)
*A61N 1/05* (2006.01)
(Continued)

(52) U.S. Cl.
CPC .......... *A61N 1/0546* (2013.01); *A61B 5/0538* (2013.01); *A61B 5/6858* (2013.01);
(Continued)

(58) Field of Classification Search
CPC .......... A61B 18/02; A61B 2018/00005; A61B 2018/00577; A61B 2018/00696;
(Continued)

(56) References Cited

U.S. PATENT DOCUMENTS

| 5,697,536 A | 12/1997 | Eggers et al. |
| 5,697,882 A | 12/1997 | Eggers et al. |

(Continued)

FOREIGN PATENT DOCUMENTS

| EP | 2929852 | 10/2015 |
| WO | WO2015013252 | 1/2015 |

(Continued)

OTHER PUBLICATIONS

Ikeda et al., "Effect of resection of the posterior nasal nerve on functional and morphological changes in the inferior turbinate mucosa," Acta Oto-Laryngologica, 128, 2008, pp. 1337-1341.
(Continued)

*Primary Examiner* — Allen Porter
(74) *Attorney, Agent, or Firm* — Perkins Coie LLP

(57) ABSTRACT

Devices, systems, and methods for specializing, monitoring, and/or evaluating therapeutic nasal neuromodulation are disclosed herein. A targeted neuromodulation system configured in accordance with embodiments of the present technology can include, for example, an evaluation/modulation assembly at a distal portion of a shaft and including a plurality of electrodes. The electrodes are configured to emit stimulating energy at frequencies for identifying and locating target neural structures and detect the resultant bioelectric properties of the tissue. The system can also include a
(Continued)

console that maps locations of the target neural structures. The evaluation/modulation assembly can then apply therapeutic neuromodulation energy in a highly tailored neuromodulation pattern based on the mapped locations of the target neural structures. Accordingly, the system provides therapeutic neuromodulation to highly specific target structures while avoiding non-target structures to reduce collateral effects.

22 Claims, 10 Drawing Sheets

Related U.S. Application Data

(60) Provisional application No. 62/421,135, filed on Nov. 11, 2016.

(51) Int. Cl.
*A61B 5/00* (2006.01)
*A61B 5/053* (2006.01)
*A61B 18/14* (2006.01)
*A61N 1/36* (2006.01)
*A61B 18/02* (2006.01)
*A61B 18/00* (2006.01)
*A61N 7/00* (2006.01)

(52) U.S. Cl.
CPC ...... *A61B 18/1492* (2013.01); *A61N 1/36075* (2013.01); *A61N 1/36135* (2013.01); *A61B 2018/00267* (2013.01); *A61B 2018/00327* (2013.01); *A61B 2018/00404* (2013.01); *A61B 2018/00434* (2013.01); *A61B 2018/00577* (2013.01); *A61B 2018/00839* (2013.01); *A61B 2018/0212* (2013.01); *A61N 1/3603* (2017.08); *A61N 1/36021* (2013.01); *A61N 2007/0021* (2013.01)

(58) Field of Classification Search
CPC ........... A61B 2018/00714; A61B 2018/00738; A61B 34/00; A61B 2034/104; A61B 18/04
See application file for complete search history.

(56) References Cited

U.S. PATENT DOCUMENTS

| | | | |
|---|---|---|---|
| 5,746,224 A | 5/1998 | Edwards | |
| 5,843,026 A * | 12/1998 | Edwards | A61B 18/00 604/508 |
| 7,608,275 B2 | 10/2009 | Deem et al. | |
| 7,655,243 B2 | 2/2010 | Deem et al. | |
| 8,105,817 B2 | 1/2012 | Deem et al. | |
| 8,636,684 B2 | 1/2014 | Deem et al. | |
| 8,676,324 B2 | 3/2014 | Simon et al. | |
| 8,920,414 B2 | 12/2014 | Stone et al. | |
| 8,936,594 B2 | 1/2015 | Frazier | |
| 8,986,301 B2 | 3/2015 | Wolf et al. | |
| 9,072,597 B2 | 7/2015 | Frazier | |
| 9,179,964 B2 | 11/2015 | Wolf et al. | |
| 9,179,967 B2 | 11/2015 | Wolf et al. | |
| 9,237,924 B2 | 1/2016 | Wolf et al. | |
| 9,415,194 B2 | 8/2016 | Wolf | |
| 9,433,463 B2 | 9/2016 | Wolf et al. | |
| 9,452,010 B2 | 9/2016 | Wolf et al. | |
| 9,526,571 B2 | 12/2016 | Wolf et al. | |
| 9,623,247 B2 | 4/2017 | Otto et al. | |
| 9,687,288 B2 | 6/2017 | Saadat | |
| 9,687,296 B2 | 6/2017 | Wolf et al. | |
| 9,700,707 B2 | 7/2017 | Deem et al. | |
| 9,731,134 B2 | 8/2017 | Otto et al. | |
| 9,763,723 B2 | 9/2017 | Saadat | |
| 9,763,743 B2 | 9/2017 | Lin et al. | |
| 9,788,886 B2 | 10/2017 | Wolf et al. | |
| 2001/0018601 A1 | 8/2001 | Ingle et al. | |
| 2005/0240147 A1 | 10/2005 | Makower et al. | |
| 2005/0288730 A1 | 12/2005 | Deem | |
| 2006/0036237 A1 | 2/2006 | Davison et al. | |
| 2006/0106375 A1 | 5/2006 | Werneth et al. | |
| 2007/0031341 A1 | 2/2007 | DiMauro | |
| 2007/0129760 A1 | 6/2007 | Demarais | |
| 2010/0204560 A1 | 8/2010 | Salahieh | |
| 2011/0264086 A1 * | 10/2011 | Ingle | A61B 18/1492 606/33 |
| 2012/0065494 A1 * | 3/2012 | Gertner | A61B 5/055 600/411 |
| 2012/0078377 A1 | 3/2012 | Gonzales | |
| 2012/0323214 A1 | 12/2012 | Shantha | |
| 2013/0165916 A1 | 6/2013 | Mathur | |
| 2013/0274824 A1 | 10/2013 | Otto et al. | |
| 2014/0018792 A1 * | 1/2014 | Gang | A61B 18/1492 606/41 |
| 2014/0025069 A1 | 1/2014 | Willard | |
| 2014/0114233 A1 | 4/2014 | Deem | |
| 2015/0018818 A1 | 1/2015 | Willard | |
| 2015/0031946 A1 | 1/2015 | Ewers | |
| 2015/0066006 A1 | 3/2015 | Srivastava | |
| 2015/0119881 A1 | 4/2015 | Jameson | |
| 2015/0164571 A1 | 6/2015 | Saadat | |
| 2015/0182282 A1 | 7/2015 | Zemel et al. | |
| 2016/0015450 A1 | 1/2016 | Wolf et al. | |
| 2016/0045277 A1 | 2/2016 | Lin | |
| 2016/0120598 A1 * | 5/2016 | Brink | A61B 18/1492 606/34 |
| 2016/0287315 A1 | 10/2016 | Wolf et al. | |
| 2016/0331459 A1 | 11/2016 | Townley | |
| 2017/0095288 A1 | 4/2017 | Wolf et al. | |
| 2017/0209199 A1 | 7/2017 | Wolf et al. | |
| 2017/0231651 A1 | 8/2017 | Dinger et al. | |
| 2017/0245924 A1 | 8/2017 | Wolf et al. | |
| 2017/0252089 A1 | 9/2017 | Hester et al. | |
| 2017/0252100 A1 | 9/2017 | Wolf et al. | |
| 2017/0266422 A1 | 9/2017 | Deem et al. | |
| 2018/0103994 A1 | 4/2018 | Fox et al. | |

FOREIGN PATENT DOCUMENTS

| | | |
|---|---|---|
| WO | WO2016134264 | 8/2016 |
| WO | WO2016183337 | 11/2016 |
| WO | WO2018087601 | 5/2018 |

OTHER PUBLICATIONS

International Search Report and Written Opinion for International Application No. PCT/US2016/032132 filed May 12, 2016, Applicant: National University of Ireland Galway, dated Nov. 14, 2016, 26 pages.
Kanaya et al., "Endoscopic posterior nasal neurectomy: an alternative to Vidian neurectomy," Clinical and Experimental Allergy Reviews, 2009, pp. 24-27.
Kikawada et al., "Endoscopic posterior nasal neurectomy: An alternative to vidian neurectomy," Operative Techniques in Otolaryngology, vol. 18, No. 4, Dec. 2007, 5 pages.
Kobayashi et al., "Resection of peripheral branches of the posterior nasal nerve compared to conventional posterior neurectomy in severe allergic rhinitis," Auris Nasus Larynx. 29 (2012), pp. 593-596.
Lin et al., "Long-term results of radiofrequency turbinoplasty for allergic rhinitis refractory to medical therapy," Arch Otolaryngol Head Neck Surg, vol. 136, No. 9, Sep. 2010, 4 pages.
Lin et al., "Radiofrequency for the treatment of allergic rhinitis refractory to medical therapy," The Laryngoscope, 113, Apr. 2003, pp. 673-678.
International Search Report and Written Opinion for International Application No. PCT/IB2017/001541 filed Nov. 11, 2017, Applicant: National University of Ireland Galway, dated Apr. 3, 2018, 15 pages.

\* cited by examiner

DEVICES, SYSTEMS, AND METHODS FOR SPECIALIZING, MONITORING, AND/OR EVALUATING THERAPEUTIC NASAL NEUROMODULATION

CROSS-REFERENCE TO RELATED APPLICATIONS

The present application is a continuation application of U.S. patent application Ser. No. 16/692,746, filed Nov. 22, 2019, entitled DEVICES, SYSTEMS, AND METHODS FOR SPECIALIZING, MONITORING, AND/OR EVALUATING THERAPEUTIC NASAL NEUROMODULATION, which is a continuation application of U.S. patent application Ser. No. 15/811,449, filed Nov. 13, 2017, entitled DEVICES, SYSTEMS, AND METHODS FOR SPECIALIZING, MONITORING, AND/OR EVALUATING THERAPEUTIC NASAL NEUROMODULATION, which claims the benefit of U.S. Provisional Patent Application No. 62/421,135, filed Nov. 11, 2016, all of which are incorporated by reference herein in their entireties.

TECHNICAL FIELD

The present technology relates generally to devices, systems, and methods for mapping, monitoring, and/or evaluation of anatomical structures, including neural structures, in or associated with a nasal region of a patient. In particular, various embodiments of the present technology are related to devices, systems, and methods for specializing, monitoring, and/or evaluating therapeutic nasal neuromodulation.

BACKGROUND

Rhinosinusitis is characterized as an inflammation of the mucous membrane of the nose and refers to a group of conditions, including allergic rhinitis, non-allergic rhinitis, chronic rhinitis, chronic sinusitis, and medical resistant rhinitis. Symptoms of rhinosinusitis include nasal blockage, obstruction, congestion, nasal discharge (e.g., rhinorrhea and/or posterior nasal drip), facial pain, facial pressure, and/or reduction or loss of smell. Allergic rhinitis can include further symptoms, such as sneezing, watery rhinorrhea, nasal itching, and itchy or watery eyes. Severe rhinitis can lead to exacerbation of coexisting asthma, sleep disturbances, and impairment of daily activities. Depending on the duration and type of systems, rhinosinusitis can fall within four subtypes: acute rhinosinusitis, recurrent rhinosinusitis, chronic rhinosinusitis with nasal polyposis (i.e., soft, non-cancerous growths on the lining of the nasal passages or sinuses), and chronic rhinosinusitis without nasal polyposis. Acute rhinosinusitis refers to symptoms lasting for less than twelve weeks, whereas chronic rhinosinusitis (with and without nasal polyposis) refers to symptoms lasting longer than twelve weeks. Recurrent rhinosinusitis refers to four or more episodes of acute rhinosinusitis within a twelve-month period, with resolution of symptoms between each episode.

There are numerous environmental and biological causes of rhinosinusitis. Non-allergic rhinosinusitis, for example, can be caused by environmental irritants (e.g., exhaust fumes, cleaning solutions, latex, perfume, dust, etc.), medications (e.g., NSAIDs, oral contraceptives, blood pressure medications including ACE inhibitors, antidepressants, etc.), foods (e.g., alcoholic beverages, spicy foods, etc.), hormonal changes (e.g., pregnancy and menstruation), and/or nasal septum deviation. Triggers of allergic rhinitis can include exposure to seasonal allergens (e.g., exposure to environmental allergens at similar times each year), perennial allergens that occur any time of year (e.g., dust mites, animal dander, molds, etc.), and/or occupational allergens (e.g., certain chemicals, grains, latex, etc.).

The treatment of rhinosinusitis can include a general avoidance of rhinitis triggers, nasal irrigation with a saline solution, and/or drug therapies. Pharmaceutical agents prescribed for rhinosinusitis include, for example, oral H1 antihistamines, topical nasal H1 antihistamines, topical intranasal corticosteroids, systemic glucocorticoids, injectable corticosteroids, anti-leukotrienes, nasal or oral decongestants, topical anticholinergic, chromoglycate, and/or anti-immunoglobulin E therapies. However, these pharmaceutical agents have limited efficacy (e.g., 17% higher than placebo or less) and undesirable side effects, such as sedation, irritation, impairment to taste, sore throat, dry nose, epistaxis (i.e., nose bleeds), and/or headaches. Immunotherapy, including sublingual immunotherapy ("SLIT"), has also been used to treat allergic rhinitis by desensitizing the patient to particular allergens by repeated administration of an allergen extract. However, immunotherapy requires an elongated administration period (e.g., 3-5 years for SLIT) and may result in numerous side effects, including pain and swelling at the site of the injection, urticarial (i.e., hives), angioedema, asthma, and anaphylaxis.

Surgical interventions have also been employed in an attempt to treat patients with drug therapy resistant, severe rhinitis symptoms. In the 1960's through 1980's, surgeries were performed to sever parasympathetic nerve fibers in the vidian canal to decrease parasympathetic tone in the nasal mucosa. More recent attempts at vidian neurectomies were found to be 50-88% effective for the treatment of rhinorrhea, with other ancillary benefits including improvements in symptoms of sneezing and nasal obstruction. These symptomatic improvements have also been correlated to histologic mucosal changes with reductions in stromal edema, eosinophilic cellular infiltration, mast cell levels, and histamine concentrations in denervated mucosa. However, despite the clinical and histologic efficacy of vidian neurectomy, resecting the vidian nerve failed to gain widespread acceptance largely due to the morbidities associated with its lack of anatomic and autonomic selectivity. For example, the site of neurectomy includes preganglionic secretomotor fibers to the lacrimal gland, and therefore the neurectomy often resulted in the loss of reflex tearing, i.e., lacrimation, which in severe cases can cause vision loss. Due to such irreversible complications, this technique was not more widely adopted. Further, due passage of postganglionic pterygopalatine fibers through the retro-orbital plexus, the position of the vidian neurectomy relative to the target end organ (i.e., the nasal mucosa) may result in re-innervation via the autonomic plexus and otic ganglion projections traveling with the accessory meningeal artery, thereby negating the clinical benefits of the neurectomy.

The complications associated with vidian neurectomies are generally attributed to the nonspecific site of autonomic denervation. Consequently, surgeons have recently shifted the site of the neurectomy to postganglionic parasympathetic rami that may have the same physiologic effect as a vidian neurectomy, while avoiding collateral injury to the lacrimal and sympathetic fibers. For example, surgeons in Japan have performed transnasal inferior turbinate submucosal resections in conjunction with resections of the posterior nasal nerves ("PNN"), which are postganglionic neural pathways located further downstream than the vidian nerve. (See, Kobayashi T, Hyodo M, Nakamura K, Komobuchi H, Honda N, Resection of peripheral branches of the posterior nasal nerve compared to conventional posterior neurectomy in severe allergic rhinitis. *Auris Nasus Larynx.* 2012 Feb. 15; 39:593-596.) The PNN neurectomies are performed at the sphenopalatine foramen, where the PNN is thought to enter the nasal region. These neurectomies are highly complex and laborious because of a lack of good surgical markers for identifying the desired posterior nasal nerves and, even if the desired nerves are located, resection of the nerves is very difficult because the nerves must be separated from the surrounding vasculature (e.g., the sphenopalatine artery).

BRIEF DESCRIPTION OF THE DRAWINGS

Many aspects of the present technology can be better understood with reference to the following drawings. The components in the drawings are not necessarily to scale. Instead, emphasis is placed on illustrating clearly the principles of the present technology. For ease of reference, throughout this disclosure identical reference numbers may be used to identify identical or at least generally similar or analogous components or features.

DETAILED DESCRIPTION

Figure 1:
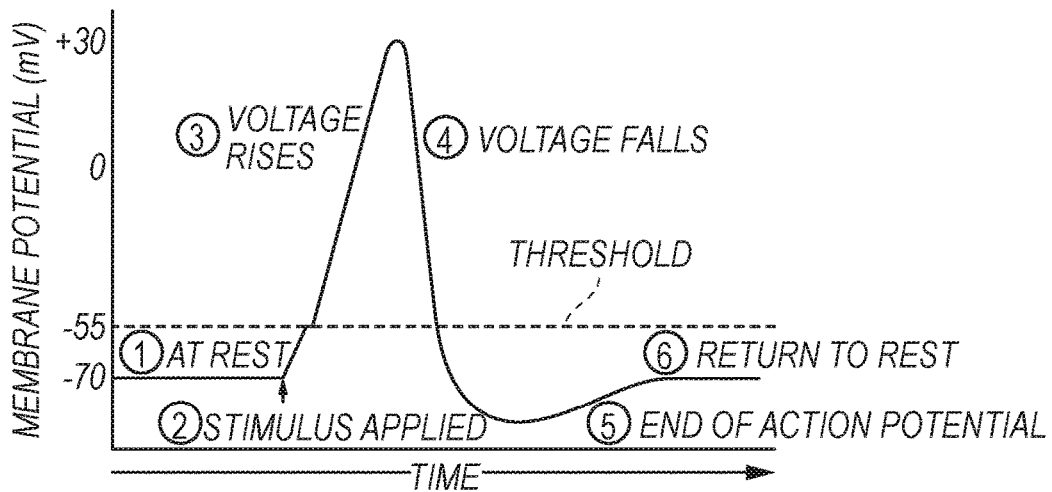
FIG. 1 is a graph illustrating an action potential of a nerve.

The devices, systems, and methods of the present technology are configured to determine one or more physiological parameters before, during, and/or after therapeutic nasal neuromodulation for (1) identifying a treatment location, (2) tailoring the treatment to a particular patient's anatomy and/or physiology, (3) adjusting ongoing treatment in real-time, and/or (4) evaluating treatment efficacy. The targeted neural ablation provided by the systems and methods described herein are expected to enhance the efficacy of the neuromodulation therapy and avoid undesired collateral effects. In several embodiments, the devices, systems, and methods disclosed herein are configured to measure the functional/pathophysiological-specific electric, and/or dielectric properties (i.e., bioelectrical properties or parameters) of shallow heterogeneous tissue, individual cellular components, and/or constituents therein on a high resolution spatial grid.

Specific details of several embodiments of the present technology are described herein with reference to FIGS. 1-9. Although many of the embodiments are described with respect to devices, systems, and methods for mapping, evaluating, and therapeutically modulating neural structures in the nasal region for the treatment of rhinitis, other applications and other embodiments in addition to those described herein are within the scope of the present technology. For example, at least some embodiments of the present technology may be useful for neural mapping and evaluation at other anatomical sites and/or the treatment of other indications (e.g., chronic sinusitis and epistaxis). It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology. The headings provided herein are for convenience only and should not be construed as limiting the subject matter disclosed.

Definitions

As used herein, the terms "distal" and "proximal" define a position or direction with respect to a clinician or a clinician's control device (e.g., a handle of a neuromodulation catheter). The terms, "distal" and "distally" refer to a position distant from or in a direction away from a clinician or a clinician's control device along the length of device. The terms "proximal" and "proximally" refer to a position near or in a direction toward a clinician or a clinician's control device along the length of device.

As used herein, "physiological parameters" refer to, at least in part, one or more of the following: cellular composition, tissue type, anatomical landscape, bioelectrical properties or parameters, electric and dielectric measurements, impedance, resistance, voltage, current density, current frequency, membrane potential, temperature, pressure, ion concentration, neurotransmitter concentration, action potential, muscle response to stimulation, and any derivative (e.g., change in any of the foregoing, rate of change of any of the foregoing, etc.) and/or combination of the foregoing and/or as detailed herein. Bioelectrical properties or parameters refer to any measurable quantity or quality of a material (e.g., tissue) to describe the interaction between that material and an electrical or magnetic source. For example, bioelectrical parameters can include, among other parameters, resistance, reactance, complex impedance, capacitance, inductance, permittivity, conductivity, voltage, current density, current frequency, and/or derivations thereof.

As used herein, "treatment parameters" refer to one or more of the following: x, y, and/or z position of the treatment device and/or electrodes relative to the treated nerves; x, y, and/or z position of the electrodes relative to one another; shape and/or layout of the activated electrode array (e.g., ring-shaped, rectangular, etc.); shape and/or size of electrodes themselves; number of electrodes; number of treatments (within same procedure or different procedure); timing and/or activation sequence of energy delivery from a plurality of electrodes; energy delivery parameters (discussed below); polarity of electrodes; grouping of electrodes; and phase angles between voltage sources driving the electrodes.

As used herein, "energy delivery parameters" refer to amplitude, frequency, waveform, phase angle, pulse-repetition frequency, and pulse width of the applied treatment energy.

As used herein, "treatment site" refers to an anatomical location at or proximate to neural structures, such as parasympathetic fibers, sympathetic fibers, sensory fibers, A-group nerve fibers, B-group nerve fibers, C-group nerve fibers, and/or other neural structures, that are eventually targeted for neuromodulation. It will be appreciated that in certain embodiments of the present technology, the neural structures that are targeted for neuromodulation must first be identified and located by the present technology. Thus, "treatment site" refers to the anatomical location including or adjacent to the treated neural structures (e.g., within about 5 mm to about 10 mm, within about 2 mm to about 5 mm, within about 2 mm, etc.). The treatment site can also include other anatomical structures (e.g., glands) and/or avoid certain structures (e.g., vessels).

As used herein, the term "neural structure" refers to the structures associated with nerves or groups of nerves including, among other structures, neuronal bundles, axons, dendrites, cell bodies, parasympathetic fibers, sympathetic fibers, sensory fibers, A-group nerve fibers, B-group nerve fibers, and/or C-group nerve fibers.

Relevant Anatomy and Physiology

Figure 2A:
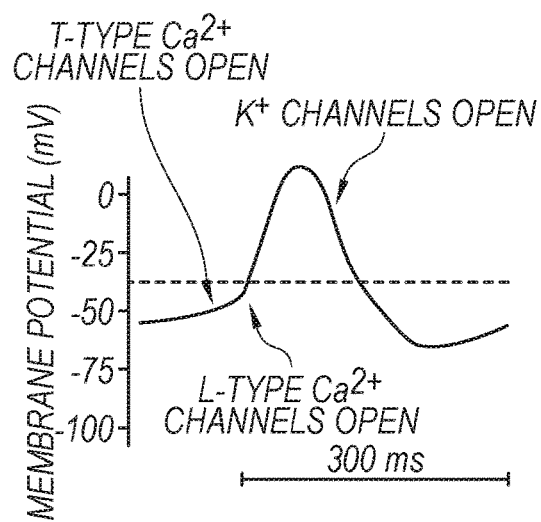
FIG. 2A is a graph illustrating neural cell membrane potential in relation to the opening of various ion channels opening.
Figure 2B:
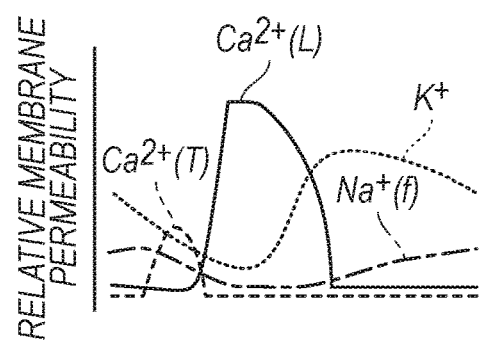
FIG. 2B is a graph illustrating relative neural cell membrane permeability.

The cell bodies, dendrites, and axons of a neuron are bounded by a cell membrane. The cell membrane includes various means for pumping sodium ions outwards. This allows the concentration of potassium ions to build up within the neuron. Because of the unequal distribution of these and other ions, the neuronal cell membrane carries an electrical charge typically up to 50 to 70 millivolts, or even greater than 70 millivolts in certain instances, with the negative charge on the inner face of the cell membrane. If the membrane is briefly short-circuited by a change in its ionic permeability, sodium ions rush inwards and potassium ions rush outwards for a brief instant. This rapid movement of ions short-circuits an adjacent region of the cell membrane so that the cycle is propagated along the membrane. This self-propagating ionic and electrical change is known as an action potential. An example of an action potential is shown in FIG. 1, and the effect of various ions channels and/or transporters opening during the compound action potential is shown in FIG. 2A. Further, FIG. 2B illustrates the effects of the compound action potential on the permeability of specific ion channels. As described in further detail below, the neuromodulation and mapping systems described herein can be used to selectively target certain ion channels to map the ensuing action potential cascade and/or neuromodulate the specific ion channel to stop the subsequent action potentials (e.g., by transmitting a stimulating or modulating signal having a threshold frequency associated with the target). Once an action potential has passed a region of a membrane, an equilibrium is restored so that the neuron is ready for the next action potential. During this brief restoration period (known as the refractory period) the membrane does not respond to any further stimuli. Action potentials are normally carried in only one direction, which is away from the origin of the action potential. All action potentials are identical after initiation. Thus, the information carried by the neurons is coded by the number and frequency pattern of the action potentials.

F wave is phenomena defined by the second of two voltage changes observed after electrical stimulation is applied to a nerve and can be used to measure nerve conduction velocity and/or other physiological parameters. For example, an electrical stimulus can be applied at a distal portion of a nerve so that the impulse travels both distally (orthodromic, i.e., towards a muscle fiber) and proximally (antidromic, i.e., back to ganglionic bodies of the motor neurons of the central nervous system (CNS)). When the orthodromic stimulus reaches the muscle fiber, it elicits a first, strong response (muscle contraction). When the antidromic stimulus reaches the motor neuron cell bodies, some of the motor neurons backfire to cause a counterflow orthodromic wave that travels distally down the nerve towards the muscle. This stimulus evokes a small, second compound muscle action potential that defines the F wave.

Epithelia form a tight monolayer harboring a stable and sufficient transepithelial resistance. The active secretion or absorption of charged salts, such as sodium ($Na^+$) and chloride ($Cl^-$) ions, induces a potential difference across the epithelial surface that can be measured as a voltage. For example, the bioelectric potential can be measured by using a high-impedance voltmeter between two electrodes of a neuromodulation device, such as the neuromodulation device described below, or a separate voltage monitoring device.

In some embodiments, the incident electromagnetic field (e.g., detected via the electrodes) with soft and hard tissues within the nasal, paranasal space (e.g., the nasal mucosa, sub-mucosa composition, periosteum, and bony plates) depends on the local geometry and the dielectric properties of those systems. Due to the structures of the soft and hard tissues, large distinctions exist in both the relative conductivity and the relative permittivity of the soft and hard tissues. As such, a threshold level of frequency can be identified to differentiate the "deeper" mucosal tissue on the turbinates from the "shallow" tissue off the turbinates.

Figure 3A:
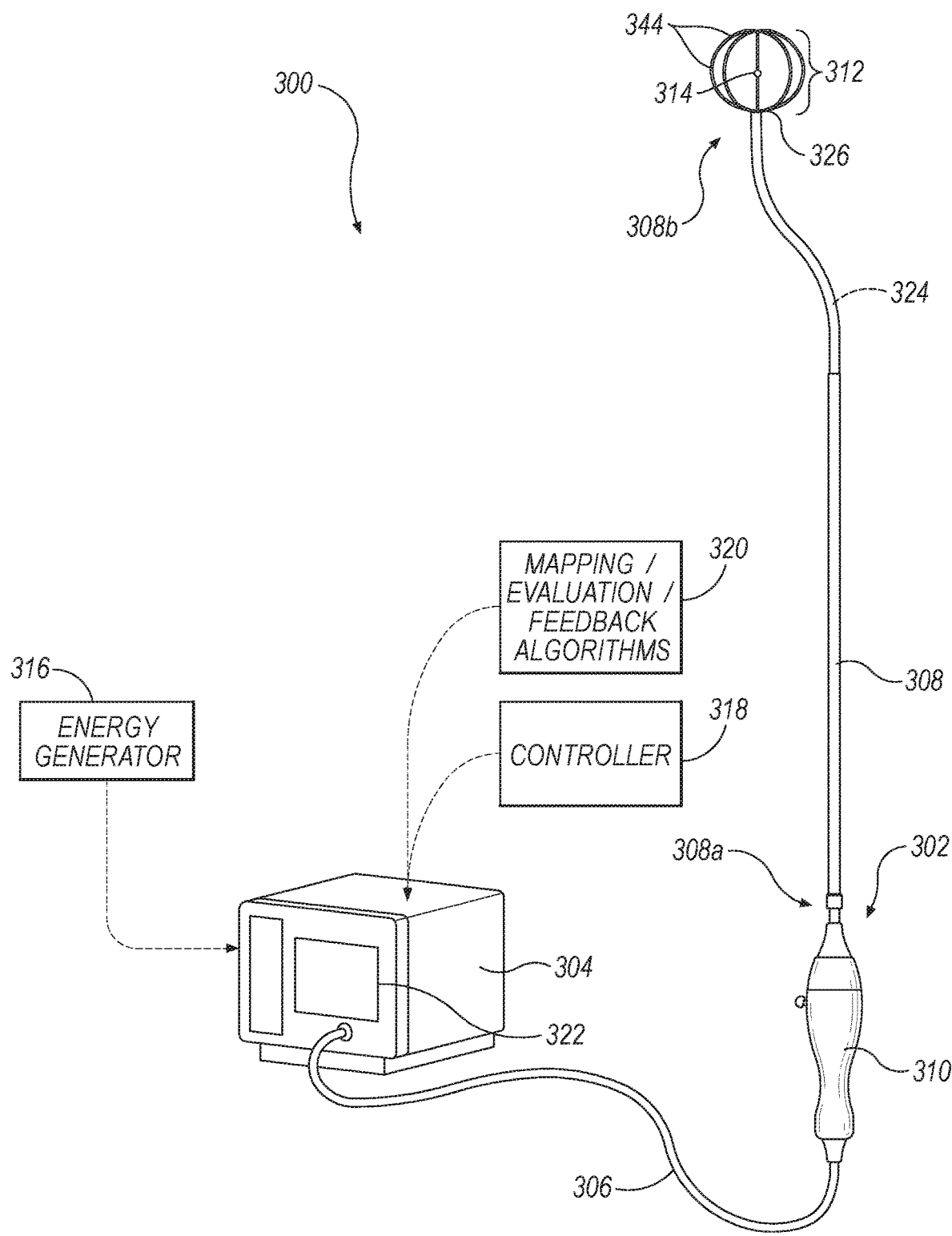
FIG. 3A is a partially schematic view of a neuromodulation and mapping system configured in accordance with embodiments of the present technology.
Figure 3B:
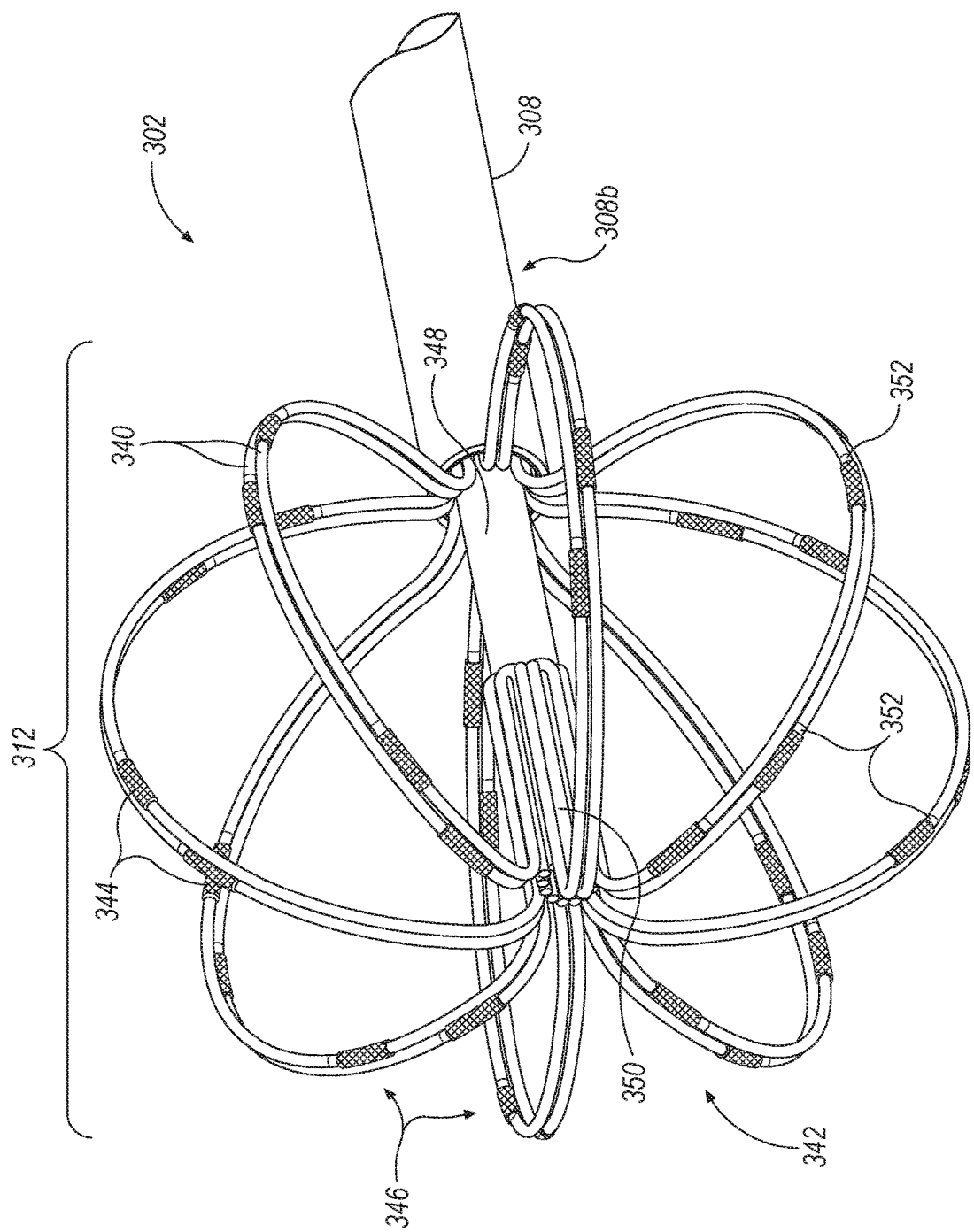
FIG. 3B is an enlarged isometric view of a distal portion of a neuromodulation and mapping device of the neuromodulation and mapping system of FIG. 3A configured in accordance with embodiments of the present technology.

Selected Embodiments of Systems for Anatomical Mapping and Therapeutic Neuromodulation FIG. 3A is a partially schematic view of a system 300 for detecting anatomical structures and therapeutic nasal neuromodulation configured in accordance with an embodiment of the present technology, and FIG. 3B is an enlarged isometric view of a distal portion of the system 300 configured in accordance with an embodiment of the present technology. As shown in FIG. 3A, the system 300 includes a detection and modulation catheter or device 302 ("device 302"), a console 304, and a cable 306 extending therebetween. The device 302 includes a shaft 308 having a proximal portion 308a, a distal portion 308b, a handle 310 at a proximal portion 308a of the shaft 308, and an evaluation/modulation assembly or element 312 at the distal portion 308b of the shaft 308. The shaft 308 is configured to locate the distal portion 308b intraluminally at a treatment or target site, such as within a nasal region proximate to postganglionic parasympathetic nerves that innervate the nasal mucosa. The target site may be a region, volume, or area in which the target nerves are located and may differ in size and shape depending upon the anatomy of the patient. For example, the target site may be a 3-5 $cm^2$ area inferior to the sphenopalatine foramen ("SPF"). In other embodiments, the target site may be larger, smaller, and/or located elsewhere in the nasal cavity to target the desired neural fibers. The evaluation/modulation assembly 312 can include at least one electrode 344 configured to therapeutically modulate postganglionic parasympathetic nerves via electromagnetic energy (e.g., RF energy). In certain embodiments, for example, the evaluation/modulation assembly 312 can therapeutically modulate the postganglionic parasympathetic nerves branching from the pterygopalatine ganglion and innervating the nasal region and nasal mucosa, such as parasympathetic nerves (e.g., the posterior nasal nerves) traversing the SPF, accessory foramen, and microforamina of a palatine bone. The electrodes 344 and/or other sensing elements of the evaluation/modulation assembly 312 can further be configured to detect one or more physiological parameters in an interest zone before, during, and/or after therapeutic neuromodulation for identifying the target site, targeting the treatment to the patient's anatomy, and/or evaluating the efficacy of the treatment.

In various embodiments, the evaluation/modulation assembly 312 can include one or more sensing elements 314, such as one or more of the following sensors: a pressure sensor, a temperature sensor (e.g., thermocouples, thermistors, etc.), a flow sensor (e.g., a Doppler velocity sensor, an ultrasonic flow meter, etc.), a flow rate sensor, a complex impedance sensor, a dielectric sensor, a chemical sensor, a bio-sensing element, a voltmeter, an electrochemical sensor, a hemodynamic sensor, an optical sensor, and/or other suitable sensing devices. The sensor(s) and/or the electrodes 344 can be connected to one or more wires (not shown; e.g., copper wires) extending through the shaft 308 to transmit signals to and from the electrodes 344 and/or the sensor(s). In some embodiments, the electrodes 344 and/or the sensor(s) can communicate wirelessly with various components of the system 300.

In some embodiments, the evaluation/modulation assembly 312 can include energy delivery elements configured to provide therapeutic neuromodulation using modalities other than RF energy, such as cryotherapeutic cooling, ultrasound energy (e.g., high intensity focused ultrasound ("HIFU") energy), microwave energy (e.g., via a microwave antenna), direct heating, high and/or low power laser energy, mechanical vibration, and/or optical power. In further embodiments, the evaluation/modulation assembly 312 can be configured to deliver chemicals or drugs to the target site to chemically ablate or embolize the target nerves. For example, the evaluation/modulation assembly 312 can include a needle applicator extending through an access portion of the shaft 308 and/or a separate introducer, and the needle applicator can be configured to inject a chemical into the target site to therapeutically modulate the target nerves, such as botox, alcohol, guanethidine, ethanol, phenol, a neurotoxin, or another suitable agent selected to alter, damage, or disrupt nerves.

The device 302 can be operatively coupled to the console 304 via a wired connection (e.g., via the cable 306) and/or a wireless connection. The console 304 can be configured to control, monitor, supply, and/or otherwise support operation of device 302. The console 304 can further be configured to generate a selected form and/or magnitude of energy for delivery to tissue or nerves at the target site via the evaluation/modulation assembly 312, and therefore the console 304 may have different configurations depending on the treatment modality of the device 302. For example, when device 302 is configured for electrode-based, heat-element-based, and/or transducer-based treatment, the console 304 includes an energy generator 316 configured to generate RF energy (e.g., monopolar, bipolar, or multi-polar RF energy), pulsed electrical energy, microwave energy, optical energy, ultrasound energy (e.g., intraluminally-delivered ultrasound and/or HIFU), direct heat energy, radiation (e.g., infrared, visible, and/or gamma radiation), and/or another suitable type of energy. When the device 302 is configured for cryotherapeutic treatment, the console 304 can include a refrigerant reservoir (not shown), and can be configured to supply the device 302 with refrigerant. Similarly, when the device 302 is configured for chemical-based treatment (e.g., drug infusion), the console 304 can include a chemical reservoir (not shown) and can be configured to supply the device 302 with one or more chemicals.

In some embodiments, the device 302 can further include a channel 324 extending along at least a portion of the shaft 308 and a port 326 at the distal portion 308b of the shaft in communication with the port 326. In certain embodiments, the channel 324 is a fluid pathway to deliver a fluid to the distal portion 308b of the shaft 308 via the port 326. For example, the channel 324 can deliver saline solution or other fluids to rinse the intraluminal nasal pathway during delivery of the evaluation/modulation assembly 312, flush the target site before applying therapeutic neuromodulation to the target site, and/or deliver fluid to the target site during energy delivery to reduce heating or cooling of the tissue adjacent to the electrodes 344. In other embodiments, the channel 324 allows for drug delivery to the treatment site. For example, a needle (not shown) can project through the port 326 to inject or otherwise deliver a nerve block, a local anesthetic, and/or other pharmacological agent to tissue at the target site. In some embodiments, the channel 324 allows for vapor and/or smoke removal or evacuation from the treatment site.

As further shown in FIG. 3A, the system 300 can include a controller 318 communicatively coupled to the device 302. In the illustrated embodiment, the controller 318 is housed in the console 304. In other embodiments, the controller 318 can be carried by the handle 310 of the device 302, the cable 306, an independent component, and/or another portion of the system 300. The controller 318 can be configured to initiate, terminate, and/or adjust operation of one or more components (e.g., the electrodes 344) of the device 302 directly and/or via the console 304. The controller 318 can be configured to execute an automated control algorithm and/or to receive control instructions from an operator (e.g., a clinician). For example, the controller 318 and/or other components of the console 304 (e.g., memory) can include a computer-readable medium carrying instructions, which when executed by the controller 318, cause the evaluation/modulation assembly 312 to perform certain functions (e.g., apply energy in a specific manner, detect impedance, detect temperature, detect nerve locations or anatomical structures, etc.). A memory includes one or more of various hardware devices for volatile and non-volatile storage, and can include both read-only and writable memory. For example, a memory can comprise random access memory (RAM), CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory.

The console 304 can also be configured to provide feedback to an operator before, during, and/or after a treatment procedure via mapping/evaluation/feedback algorithms 320. For example, the mapping/evaluation/feedback algorithms 320 can be configured to provide information associated with the location of nerves at the treatment site, the location of other anatomical structures (e.g., vessels) at the treatment site, the temperature at the treatment site during monitoring and modulation, and/or the effect of the therapeutic neuromodulation on the nerves at the treatment site. In certain embodiments, the mapping/evaluation/feedback algorithm 320 can include features to confirm efficacy of the treatment and/or enhance the desired performance of the system 300. For example, the mapping/evaluation/feedback algorithm 320, in conjunction with the controller 318 and the evaluation/modulation assembly 312, can be configured to monitor neural activity and/or temperature at the treatment site during therapy and automatically shut off the energy delivery when the neural activity and/or temperature reaches a predetermined threshold (e.g., a threshold reduction in neural activity, a threshold maximum temperature when applying RF energy, or a threshold minimum temperature when applying cryotherapy). In other embodiments, the mapping/evaluation/feedback algorithm 320, in conjunction with the controller 318, can be configured to automatically terminate treatment after a predetermined maximum time, a predetermined maximum impedance or resistance rise of the targeted tissue (i.e., in comparison to a baseline impedance measurement), a predetermined maximum impedance of the targeted tissue), and/or other threshold values for biomarkers associated with autonomic function. This and other information associated with the operation of the system 300 can be communicated to the operator via a display 322 (e.g., a monitor, touchscreen, user interface, etc.) on the console 304 and/or a separate display (not shown) communicatively coupled to the console 304.

In various embodiments, the evaluation/modulation assembly 312 and/or other portions of the system 300 can be configured to detect various bioelectric-parameters of the tissue at the target site, and this information can be used by the mapping/evaluation/feedback algorithms 320 to determine the anatomy at the target site (e.g., tissue types, tissue locations, vasculature, bone structures, foramen, sinuses, etc.), locate neural structures, differentiate between different types of neural structures, map the anatomical and/or neural structure at the target site, and/or identify neuromodulation patterns of the evaluation/modulation assembly 312 with respect to the patient's anatomy. For example, the evaluation/modulation assembly 312 can be used to detect resistance, complex electrical impedance, dielectric properties, temperature, and/or other properties that indicate the presence of neural fibers and/or other anatomical structures in the target region. In certain embodiments, the evaluation/modulation assembly 312, together with the mapping/evaluation/feedback algorithms 320, can be used to determine resistance (rather than impedance) of the tissue (i.e., the load) to more accurately identify the characteristics of the tissue. The mapping/evaluation/feedback algorithms 320 can determine resistance of the tissue by detecting the actual power and current of the load (e.g., via the electrodes 344). In some embodiments, the system 300 provides resistance measurements with a high degree of accuracy and a very high degree of precision, such as precision measurements to the hundredths of an Ohm (e.g., 0.01Ω) for the range of 1-50Ω The high degree of resistance detection accuracy provided by the system 300 allows for the detection sub-microscale structures, including the firing of neural structures, differences between neural structures and other anatomical structures (e.g., blood vessels), and event different types of neural structures. This information can be analyzed by the mapping/evaluation/feedback algorithms and/or the controller 318 and communicated to the operator via a high resolution spatial grid (e.g., on the display 322) and/or other type of display to identify neural structures and other anatomy at the treatment site and/or indicate predicted neuromodulation regions based on the ablation pattern with respect to the mapped anatomy.

The device 302 provides access to target sites deep within the nasal region, such as at the immediate entrance of parasympathetic fibers into the nasal cavity to therapeutically modulate autonomic activity within the nasal cavity. In certain embodiments, for example, the device 302 can position the evaluation/modulation assembly 312 inferior to the SPF at the site of access foramen and/or microforamina as described in U.S. patent application Ser. No. 15/153,217, filed May 10, 2016, which is incorporated herein by reference in its entirety. By manipulating the proximal portion 308a of the shaft 308 from outside the entrance of the nose, a clinician may advance the shaft 308 through the tortuous intraluminal path through the nasal cavity and remotely manipulate the distal portion 308b of the shaft 308 via the handle 310 to position the evaluation/modulation assembly 312 at the target site. In certain embodiments, the shaft 308 can be a steerable device (e.g., a steerable catheter) with a small bend radius (e.g., a 5 mm bend radius, a 4 mm bend radius, a 3 mm bend radius or less) that allows the clinician to navigate through the tortuous nasal anatomy. The steerable shaft can further be configured to articulate in at least two different directions. For example, the steerable shaft 308 can include dual pull wire rings that allow a clinician to form the distal portion 308b of the shaft 308 into an "S"-shape to correspond to the anatomy of the nasal region. In other embodiments, the articulating shaft 308 can be made from a substantially rigid material (e.g., a metal material) and include rigid links at the distal portion 308b of the shaft 308 that resist deflection, yet allow for a small bend radius (e.g., a 5 mm bend radius, a 4 mm bend radius, a 3 mm bend radius or less). In further embodiments, the steerable shaft 308 may be a laser-cut tube made from a metal and/or other suitable material. The laser-cut tube can include one or more pull wires operated by the clinician to allow the clinician to deflect the distal portion 308b of the shaft 308 to navigate the tortuous nasal anatomy to the target site.

In various embodiments, the distal portion 308b of the shaft 308 is guided into position at the target site via a guidewire (not shown) using an over-the-wire (OTW) or a rapid exchange (RX) technique. For example, the distal end of the evaluation/modulation assembly 312 can include a channel for engaging the guidewire. Intraluminal delivery of the evaluation/modulation assembly 312 can include inserting the guide wire into an orifice in communication with the nasal cavity (e.g., the nasal passage or mouth), and moving the shaft 308 and/or the evaluation/modulation assembly 312 along the guide wire until the evaluation/modulation assembly 312 reaches a target site (e.g., inferior to the SPF). In further embodiments, the device 302 can be configured for delivery via a guide catheter or introducer sheath (not shown) with or without using a guide wire. Image guidance (e.g., via an endoscope, computed tomography (CT), fluoroscopy, ultrasound, optical coherence tomography (OCT), and/or combinations thereof) may be used to aid the clinician's positioning and manipulation of the distal portion 308b of the shaft 308 and the evaluation/modulation assembly 312.

During delivery to the target site, the evaluation/modulation assembly 312 can be arranged in a low-profile delivery state and, once at the target site, the evaluation/modulation assembly 312 can be transformed to an expanded state (shown in FIGS. 3A and 3B) via manipulation of the handle 310 such that the evaluation/modulation assembly 312 contacts tissue at the target site for physiological parameter detection and/or neural modulation. As shown in the enlarged view of the evaluation/modulation assembly 312 in FIG. 3B, the evaluation/modulation assembly 312 can include a plurality of struts 340 that are spaced apart from each other to form a frame or basket 342 when the evaluation/modulation assembly 312 is in the expanded state. The struts 340 can carry one or more of the electrodes 344 and/or other energy delivery elements. In the expanded state, the struts 340 can position at least two of the electrodes 344 against tissue at a target site or zone of interest within the nasal region (e.g., proximate to the palatine bone inferior to the SPF). The electrodes 344 can apply bipolar or multipolar radiofrequency (RF) energy to the target site to detect bioelectric properties of the treatment site and/or to therapeutically modulate postganglionic parasympathetic nerves that innervate the nasal mucosa proximate to the target site. In various embodiments, the electrodes 344 can be configured to apply pulsed RF energy with a desired duty cycle (e.g., 1.00 second on/0.50 seconds off), varying power levels, and/or varying pulse durations and frequency to regulate the temperature increase in the target tissue. As shown in FIG. 3B, the distal end portion of the basket includes a double inflection to enhance or maximize the contact surface area of the strut 340 to adjacent tissue (e.g., a mucosal wall).

In the embodiment illustrated in FIG. 3B, the basket 342 includes eight branches 346 spaced radially apart from each other to form at least a generally spherical structure, and each of the branches 346 includes two struts 340 positioned adjacent to each other. In other embodiments, however, the basket 342 can include fewer than eight branches 346 (e.g., two, three, four, five, six, or seven branches) or more than eight branches 346. In further embodiments, each branch 346 of the basket 342 can include a single strut 340, more than two struts 340, and/or the number of struts 340 per branch 346 can vary. In still further embodiments, the branches 346 and struts 340 can form baskets or frames having other suitable shapes for placing the electrodes 344 in contact with tissue at the target site. For example, when in the expanded state, the struts 340 can form an ovoid shape, a hemispherical shape, a cylindrical structure, a pyramid structure, and/or other suitable shapes. The structural shape of the basket 342 can also be segmented, replicated, and/or miniaturized duplications of one or more suitable shapes.

As shown in FIG. 3B, the evaluation/modulation assembly 312 can further include an internal or interior support member 348 that extends distally from the distal portion 308b of the shaft 308. A distal end portion 350 of the support member 348 can support the distal end portions of the struts 340 to form the desired basket shape. For example, as shown in FIG. 3, the struts 340 can extend distally from the distal portion 308b of the shaft 308 and the distal end portions of the struts 340 can attach to the distal end portion 350 of the support member 348. In certain embodiments, the support member 348 can include an internal channel (not shown) through which flexible electrical connectors (e.g., wires) coupled to the electrodes 344 and/or other electrical features of the evaluation/modulation assembly 312 can run. In various embodiments, the internal support member 348 can also carry an electrode (not shown) at the distal end portion 350 and/or along the length of the support member 348.

The individual struts 340 can be made from a resilient material, such as a shape-memory material (e.g., Nitinol), that allows the struts 340 to self-expand into the desired shape of the basket 342 when in the expanded state. The struts 340 can also be made from composite wire structures with enhanced core materials for conductivity and resistivity performance to enhance the signals detected by the electrodes 344. In other embodiments, the struts 340 can be made from other suitable materials and/or the evaluation/modulation assembly 312 can be mechanically expanded via a balloon or by proximal movement of the support member 348. The basket 342 and the associated struts 340 can have sufficient rigidity to support the electrodes 344 and position or press the electrodes 344 against tissue at the target site. In addition, the expanded basket 342 can press against surrounding anatomical structures proximate to the target site (e.g., the turbinates, the palatine bone, etc.) and the individual struts 340 can at least partially conform to the shape of the adjacent anatomical structures to anchor the therapeutic element 312 at the treatment site during energy delivery. This expansion and conformability of the struts 340 can facilitate placing the electrodes 344 in contact with the surrounding tissue at the target site.

Each strut 340 can include one or more electrodes 344 (e.g., two electrodes 344, three electrodes 344, four electrodes 344, five electrodes 344, more than five electrodes 344), and/or the number of electrodes 344 on the different struts 340 can vary. In some embodiments, for example, each strut 340 can include five electrodes 344 such that each branch 346 includes ten electrodes 344 that can define five adjacent electrode pairs, although the electrodes 344 may be independently activated and paired with different electrodes 344 of the branch 346 and/or other branches 346. For example, the electrodes 344 can have a length of 0.25-2.25 mm (e.g., 0.75 mm), a spacing along each strut 340 of about 0.5-3.5 mm (e.g., 1.5 mm), and an inter-pairing spacing of about 1.5-4.0 mm (e.g., 2 mm). In other embodiments the electrode sizing and spacing can differ. In some embodiments, it may be beneficial to have the electrodes positioned or spaced differently along the struts 340 than shown in FIG. 3B and/or asymmetrically positioned electrodes on one or more of the struts 340. For example, a mid-portion of the struts 340 may include a higher density of electrodes 344 than the proximal or distal portions of the struts 340. Such an asymmetric distribution of electrodes 344 may be particularly advantageous for mapping functions. This may be achieved through the placing of the electrode array in a known spatial configuration, and mapping electro-anatomical characteristics in a composition of multiple (high-density) activation sequence mappings in multiple planes and/or multiple or varying depths that incorporates variations in the impedance of different tissue types, including different cellular or functional constructs, and at different waveform frequencies (as described in greater detail below).

In certain embodiments, each electrode 344 can be operated independently of the other electrodes 344. For example, each electrode can be individually activated and the polarity and amplitude of each electrode can be selected by an operator or a control algorithm executed by the controller 318 (FIG. 3A). The selective independent control of the electrodes 344 allows the evaluation/modulation assembly 312 to detect information and deliver RF energy to highly customized regions. For example, a select portion of the electrodes 344 can be activated to target specific neural fibers in a specific region while the other electrodes 344 remain inactive. In certain embodiments, for example, electrodes 344 may be activated across the portion of the basket 342 that is adjacent to tissue at the target site, and the electrodes 344 that are not proximate to the target tissue can remain inactive to avoid applying energy to non-target tissue. In addition, the electrodes 344 can be individually activated to stimulate or therapeutically modulate certain regions in a specific pattern at different times (e.g., via multiplexing), which facilitates detection of anatomical parameters across a zone of interest and/or regulated therapeutic neuromodulation.

The electrodes 344 can be electrically coupled to the energy generator 316 (FIG. 3B) via wires (not shown) that extend from the electrodes 344, through the shaft 308, and to the energy generator 316. When each of the electrodes 344 is independently controlled, each electrode 344 couples to a corresponding wire that extends through the shaft 308. This allows each electrode 344 to be independently activated for stimulation or neuromodulation to provide precise ablation patterns and/or individually detected via the console 304 (FIG. 3A) to provide information specific to each electrode 344 for neural or anatomical detection and mapping. In other embodiments, multiple electrodes 344 can be controlled together and, therefore, multiple electrodes 344 can be electrically coupled to the same wire extending through the shaft 308. The energy generator 316 (FIG. 3A) and/or components (e.g., a control module) operably coupled thereto can include custom algorithms to control the activation of the electrodes 344. For example, the RF generator can deliver RF power at about 200-300 W to the electrodes 344, and do so while activating the electrodes 344 in a predetermined pattern selected based on the position of the evaluation/modulation assembly 312 relative to the treatment site and/or the identified locations of the target nerves. In other embodiments, the energy generator 316 delivers power at lower levels (e.g., less than 1 W, 1-5 W, 5-15 W, 15-50 W, 50-150 W, etc.) for stimulation and/or higher power levels. For example, the energy generator 316 can be configured to delivery stimulating energy pulses of 1-3 W via the electrodes 344 to stimulate specific targets in the tissue.

As shown in FIG. 3B, the evaluation/modulation assembly 312 can further include one or more temperature sensors 352 disposed on the struts 340 and/or other portions of the evaluation/modulation assembly 312 and electrically coupled to the console 304 (FIG. 3A) via wires (not shown) that extend through the shaft 308. In various embodiments, the temperature sensors 352 can be positioned proximate to the electrodes 344 to detect the temperature at the interface between tissue at the target site and the electrodes 344. In other embodiments, the temperature sensors 352 can penetrate the tissue at the target site (e.g., a penetrating thermocouple) to detect the temperature at a depth within the tissue. The temperature measurements can provide the operator or the system with feedback regarding the effect of the therapeutic neuromodulation on the tissue. For example, in certain embodiments the operator may wish to prevent or reduce damage to the tissue at the treatment site (e.g., the nasal mucosa), and therefore the temperature sensors 352 can be used to determine if the tissue temperature reaches a predetermined threshold for irreversible tissue damage. Once the threshold is reached, the application of therapeutic neuromodulation energy can be terminated to allow the tissue to remain intact and avoid significant tissue sloughing during wound healing. In certain embodiments, the energy delivery can automatically terminate based on the mapping/evaluation/feedback algorithm 320 (FIG. 3A) stored on the console 304 (FIG. 3A) operably coupled to the temperature sensors 352.

In other embodiments, the evaluation/modulation assembly 312 can have different configurations than that shown in FIG. 3B. For example, the evaluation/modulation assembly 312 can include structures and components similar to those described in U.S. patent application Ser. No. 15/153,217, filed May 10, 2016, and incorporated herein in its entirety. In various embodiments, for example, the evaluation/modulation assembly 312 may include an expandable balloon that has plurality of electrodes disposed thereon with spacing selected to enhance sensing resolution. The balloon can be positioned within the basket 342 and/or be a standalone structure. The balloon may also be configured to act as a heat sink by being configured to receive a cooling agent or media to reduce the heating of tissue adjacent to the electrodes 344 during preventing the surfaces electrodes from contributing to thermal damage from ablation.

Referring to FIGS. 3A and 3B together, when the evaluation/modulation assembly 312 is positioned at the target site, therapeutic modulation may be applied via the electrodes 344 and/or other features of the evaluation/modulation assembly 312 to precise, localized regions of tissue to induce one or more desired therapeutic neuromodulating effects to disrupt parasympathetic motor sensory function. The evaluation/modulation assembly 312 can selectively target postganglionic parasympathetic fibers that innervate the nasal mucosa at a target or treatment site proximate to or at their entrance into the nasal region. For example, evaluation/modulation assembly 312 can be positioned to apply therapeutic neuromodulation at least proximate to the SPF to therapeutically modulate nerves entering the nasal region via the SPF, accessory foramen and/or microforamina (e.g., in the palatine bone). The purposeful application of the energy at the target site may achieve therapeutic neuromodulation along all or at least a portion of posterior nasal neural fibers entering the nasal region. The therapeutic neuromodulating effects are generally a function of, at least in part, power, time, and contact between the energy delivery elements and the adjacent tissue. For example, in certain embodiments therapeutic neuromodulation of autonomic neural fibers are produced by applying RF energy in pulsed or constant waveforms at a power of about 2-20 W (e.g., 5 W, 7 W, 10 W, etc.) for a time period of about 1-20 seconds (e.g., 5-10 seconds, 8-10 seconds, 10-12 seconds, etc.).

The therapeutic neuromodulating effects may include partial or complete denervation via thermal ablation and/or non-ablative thermal alteration or damage (e.g., via sustained heating and/or resistive heating). Desired thermal heating effects may include raising the temperature of target neural fibers above a desired threshold to achieve non-ablative thermal alteration, or above a higher temperature to achieve ablative thermal alteration. For example, the target temperature may be above the 45° C. isotherm in which the applicants have identified that modulations of parasympathetic nerves begin to occur. It is expected that therapeutic neuromodulation can be achieved at the 45° C. isotherm, the 55° C. isotherm, at the 60° C., isotherms between 45° C. and 60° C., and/or higher isotherms. Accordingly, the system 300 can be configured to apply therapeutic neuromodulation until the temperature at the target site reaches a threshold of 45° C., 55° C., 60° C., a value between 45° C. and 60° C., or higher than 60° C. In various embodiments, delivering the neuromodulation energy creates an electric field-depth that causes ionic agitation to disrupt neural activity and/or tissue temperatures resulting in a lesion size for changing the conductive/impedance/electrical properties of the tissue types within the region of interest.

Hypothermic effects may also provide neuromodulation. For example, a cryotherapeutic applicator may be used to cool tissue at a target site to provide therapeutically-effective direct cell injury (e.g., necrosis), vascular injury (e.g., starving the cell from nutrients by damaging supplying blood vessels), and sublethal hypothermia with subsequent apoptosis. Exposure to cryotherapeutic cooling can cause acute cell death (e.g., immediately after exposure) and/or delayed cell death (e.g., during tissue thawing and subsequent hyperperfusion). Embodiments of the present technology can include cooling a structure positioned at or near tissue such that the tissue is effectively cooled to a depth where the targeted postganglionic parasympathetic nerves reside. For example, the cooling structure is cooled to the extent that it causes therapeutically effective, cryogenic posterior nasal nerve modulation.

In certain embodiments, the system 300 can determine the locations and/or morphology of neural structures and/or other anatomical structures before therapy such that the therapeutic neuromodulation can be applied to precise regions including target neural structures, while avoiding negative effects on non-target structures, such as blood vessels. As described in further detail below, the system 300 can detect various bioelectrical parameters in an interest zone (e.g., within in the nasal cavity) to determine the location and morphology of various neural structures (e.g., different types of neural structures, neuronal directionality, etc.) and/or other tissue (e.g., glandular structures, vessels, bony regions, etc.). In some embodiments, the system 300 is configured to measure bioelectric potential. To do so, one or more of the electrodes 344 is placed in contact with an epithelial surface at a region of interest (e.g., a treatment site). Electrical stimuli (e.g., constant or pulsed currents at one or more frequencies) are applied to the tissue by one or more electrodes 344 at or near the treatment site, and the voltage and/or current differences at various different frequencies between various pairs of electrodes 344 of the evaluation/modulation assembly 312 may be measured to produce a spectral profile or map of the detected bioelectric potential, which can be used to identify different types of tissues (e.g., vessels, neural structures, and/or other types of tissue) in the region of interest. For example, current (i.e., direct or alternating current) can be applied to a pair of electrodes 344 adjacent to each other and the resultant voltages and/or currents between other pairs of adjacent electrodes 344 are measured. It will be appreciated that the current injection electrodes 344 and measurement electrodes 344 need not be adjacent, and that modifying the spacing between the two current injection electrodes 344 can affect the depth of the recorded signals. For example, closely-spaced current injection electrodes 344 provided recorded signals associated with tissue deeper from the surface of the tissue than further spaced apart current injection electrodes 344 that provide recorded signals associated with tissue at shallower depths. Recordings from electrode pairs with different spacings may be merged to provide additional information on depth and localization of anatomical structures.

Figure 6:
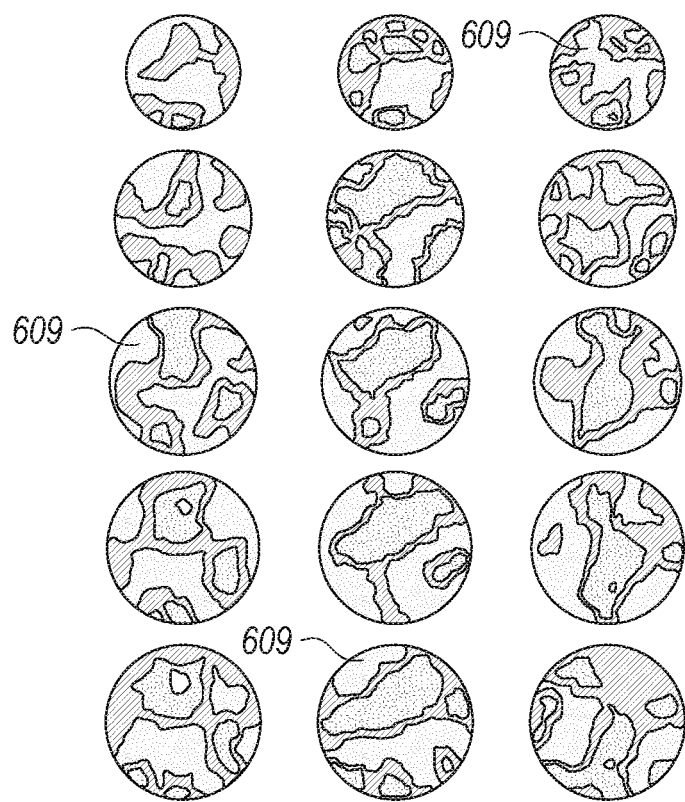
FIG. 6 is an illustration of neural mapping configured in accordance with embodiments of the present technology.

Further, complex impedance and/or resistance measurements of the tissue at the region of interest can be detected directly from current-voltage data provided by the bioelectric potential measurements while differing levels of frequency currents are applied to the tissue (e.g., via the evaluation/modulation assembly 312), and this information can be used to map the neural and anatomical structures by the use of frequency differentiation reconstruction. Applying the stimuli at different frequencies will target different stratified layers or cellular bodies or clusters. At high signal frequencies (e.g., electrical injection or stimulation), for example, cell membranes of the neural structures do not impede current flow, and the current passes directly through the cell membranes. In this case, the resultant measurement (e.g., impedance, resistance, capacitance, and/or induction) is a function of the intracellular and extracellular tissue and liquids. At low signal frequencies, the membranes impede current flow to provide different defining characteristics of the tissues, such as the shapes of the cells or cell spacing. The stimulation frequencies can be in the megahertz range, in the kilohertz range (e.g., 400-500 kHz, 450-480 kHz, etc.), and/or other frequencies attuned to the tissue being stimulated and the characteristics of the device being used. The detected complex impedance or resistances levels from the zone of interest can be displayed to the user (e.g., via the display 322) to visualize certain structures based on the stimulus frequency. For example, FIG. 6 is an illustration of neural impedance mapping at three different regions of tissue and at five different depths, with the neural structures 609 being identified by a different color or shading so that the clinician can locate suitable neural targets. Similar complex impedance mapping can be provided for different structures (e.g., vessels).

Further, the inherent morphology and composition of the anatomical structures in the nasal region react differently to different frequencies and, therefore, specific frequencies can be selected to identify very specific structures. For example, the morphology or composition of targeted structures for anatomical mapping may depend on whether the cells of tissue or other structure are membranonic, stratified, and/or annular. In various embodiments, the applied stimulation signals can have predetermined frequencies attuned to specific neural structures, such as the level of myelination and/or morphology of the myelination. For example, second axonal parasympathetic structures are poorly myelinated than sympathetic nerves or other structures and, therefore, will have a distinguishable response (e.g., complex impedance, resistance, etc.) with respect to a selected frequency than sympathetic nerves. Accordingly, applying signals with different frequencies to the target site can distinguish the targeted parasympathetic nerves from the non-targeted sensory nerves, and therefore provide highly specific target sites for neural mapping before or after therapy and/or neural evaluation post-therapy. In some embodiments, the neural and/or anatomical mapping includes measuring data at a region of interest with at least two different frequencies to identify certain anatomical structures such that the measurements are taken first based on a response to an injection signal having a first frequency and then again based on an injection signal having a second frequency different from the first. For example, there are two frequencies at which hypertrophied (i.e., disease-state characteristics) sub-mucosal targets have a different electrical conductivity or permittivity compared to "normal" (i.e., healthy) tissue. Complex conductivity may be determined based on one or more measured physiological parameters (e.g., complex impedance, resistance, dielectric measurements, dipole measurements, etc.) and/or observance of one or more confidently known attributes or signatures. Furthermore, the system 300 can also apply neuromodulation energy via the electrodes 344 at one or more predetermined frequencies attuned to a target neural structure to provide highly targeted ablation of the selected neural structure associated with the frequency(ies). This highly targeted neuromodulation also reduces the collateral effects of neuromodulation therapy to non-target sites/structures (e.g., blood vessels) because the targeted signal (having a frequency tuned to a target neural structure) will not have the same modulating effects on the non-target structures.

Accordingly, bioelectric properties, such as complex impedance and resistance, can be used by the system 300 before, during, and/or after neuromodulation therapy to guide one or more treatment parameters. For example, before, during, and/or after treatment, impedance or resistance measurements may be used to confirm and/or detect contact between one or more electrodes 344 and the adjacent tissue. The impedance or resistance measurements can also be used to detect whether the electrodes 344 are placed appropriately with respect to the targeted tissue type by determining whether the recorded spectra have a shape consistent with the expected tissue types and/or whether serially collected spectra were reproducible. In some embodiments, impedance or resistance measurements may be used to identify a boundary for the treatment zone (e.g., specific neural structures that are to be disrupted), anatomical landmarks, anatomical structures to avoid (e.g., vascular structures or neural structures that should not be disrupted), and other aspects of delivering energy to tissue.

The bioelectric information can be used to produce a spectral profile or map of the different anatomical features tissues at the target site, and the anatomical mapping can be visualized in a 3D or 2D image via the display 322 and/or other user interface to guide the selection of a suitable treatment site. This neural and anatomical mapping allows the system 300 to accurately detect and therapeutically modulate the postganglionic parasympathetic neural fibers that innervate the mucosa at the numerous neural entrance points into the nasal cavity. Further, because there are not any clear anatomical markers denoting the location of the SPF, accessory foramen, and microforamina, the neural mapping allows the operator to identify and therapeutically modulate nerves that would otherwise be unidentifiable without intricate dissection of the mucosa. In addition, anatomical mapping also allows the clinician to identify certain structures that the clinician may wish to avoid during therapeutic neural modulation (e.g., certain arteries). The neural and anatomical bioelectric properties detected by the system 300 can also be used during and after treatment to determine the real-time effect of the therapeutic neuromodulation on the treatment site. For example, the mapping/evaluation/feedback algorithms 320 can also compare the detected neural locations and/or activity before and after therapeutic neuromodulation, and compare the change in neural activity to a predetermined threshold to assess whether the application of therapeutic neuromodulation was effective across the treatment site.

In various embodiments, the system 300 can also be configured to map the expected therapeutic modulation patterns of the electrodes 344 at specific temperatures and, in certain embodiments, take into account tissue properties based on the anatomical mapping of the target site. For example, the system 300 can be configured to map the ablation pattern of a specific electrode ablation pattern at the 45° C. isotherm, the 55° C. isotherm, the 65° C. isotherm, and/or other temperature/ranges (e.g., temperatures ranging from 45° C. to 70° C. or higher) depending on the target site and/or structure.

Figure 4A:
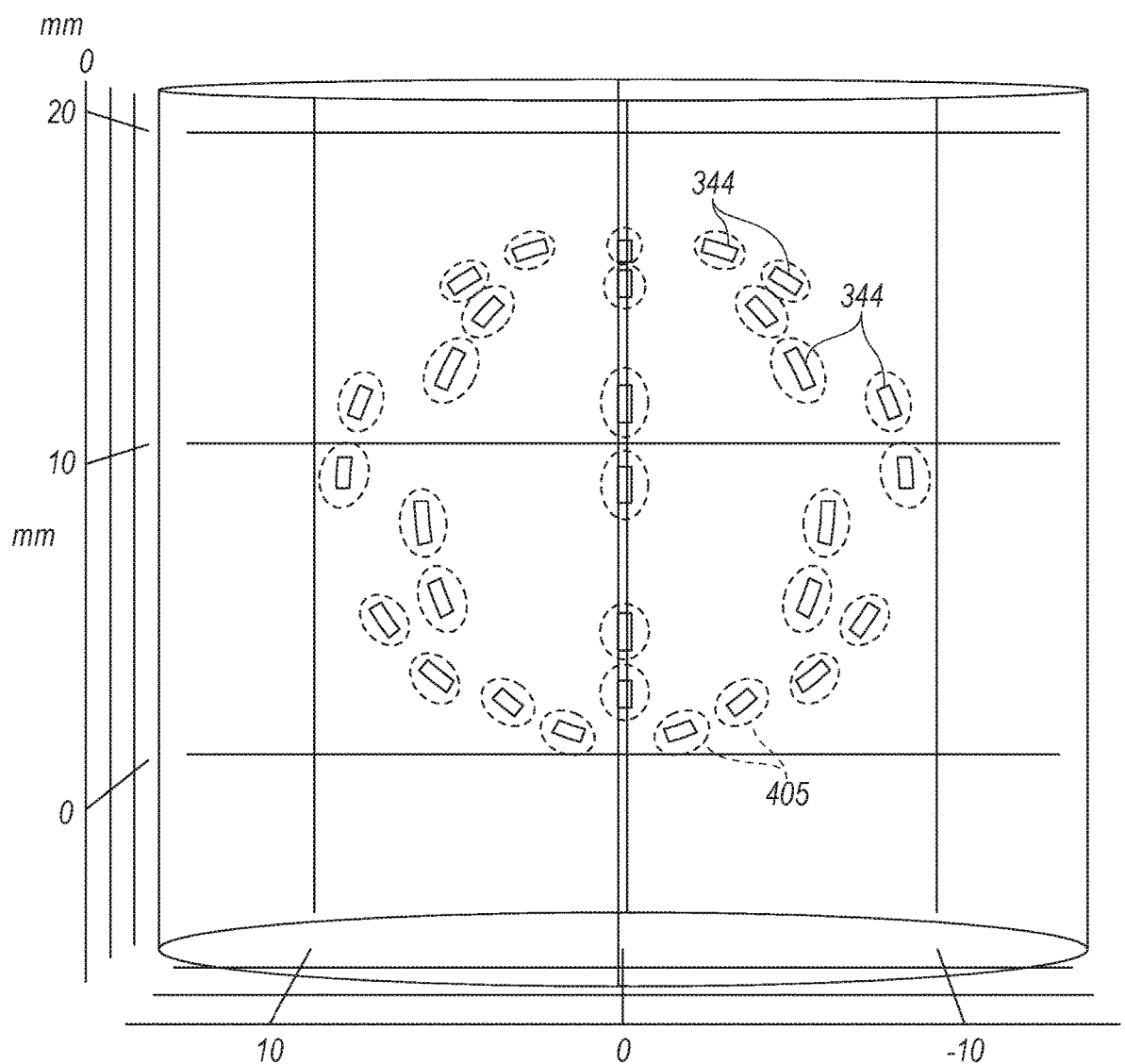
FIGS. 4A-4C are three dimensional views of projected electrode ablation patterns of a neuromodulation device configured in accordance with embodiments of the present technology.
Figure 4B:
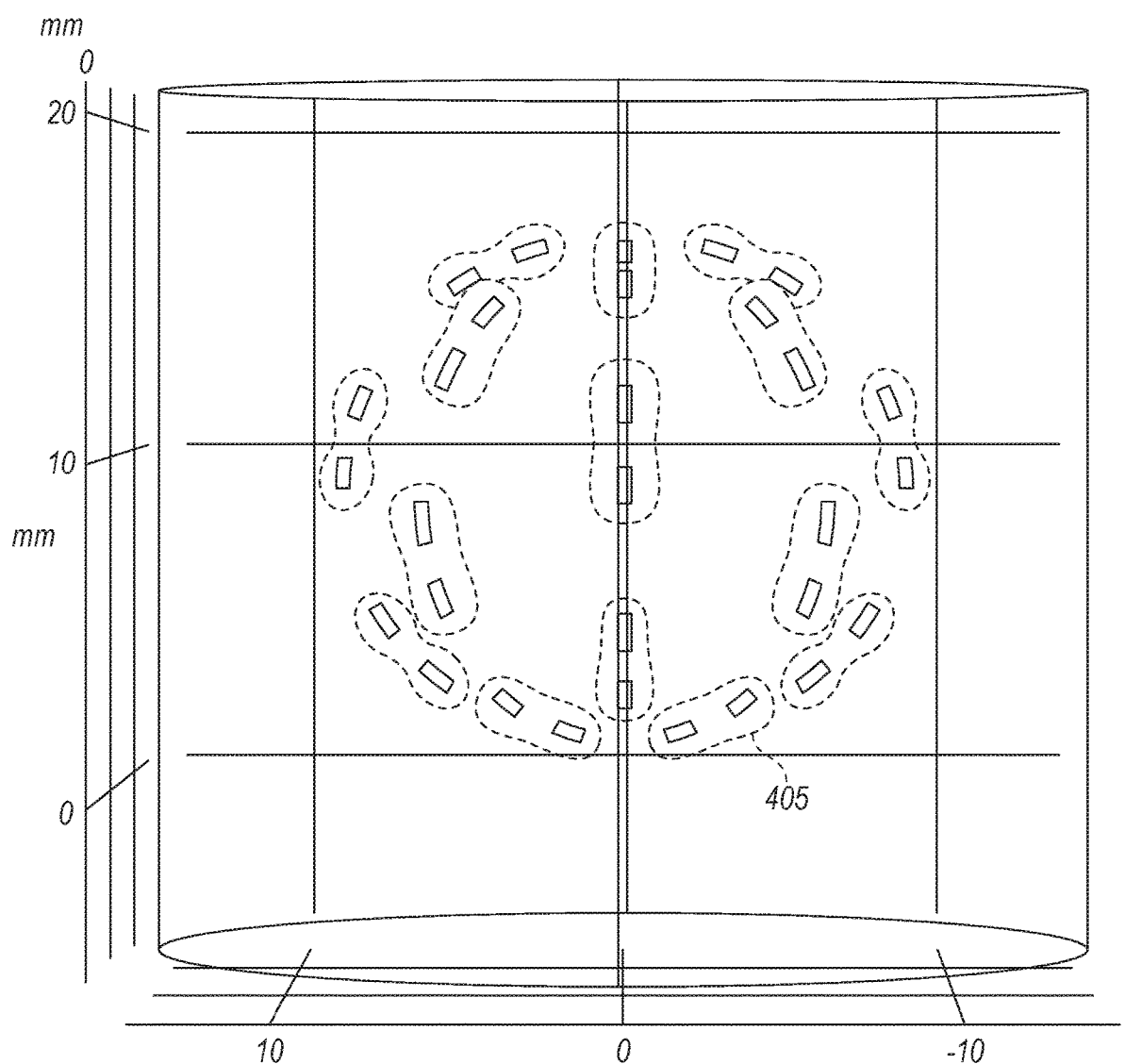
Figure 4C:
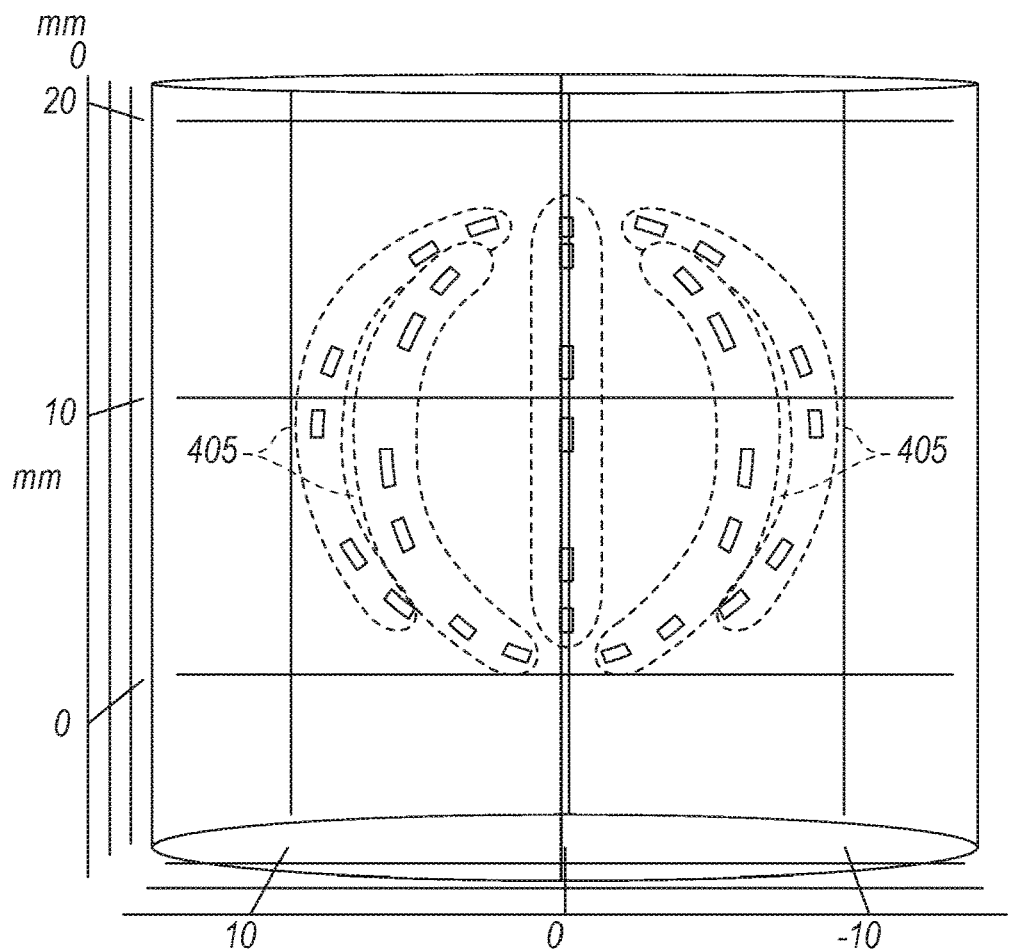

FIGS. 4A-4C illustrate three-dimensional views of such projected ablation patterns of the electrodes 344 of the evaluation/modulation assembly 312 (FIG. 3A) configured in accordance with embodiments of the present technology. The ablation pattern mapping defines a region of influence 405 (shown in broken lines) that each electrode 344 has on the surrounding tissue. The region of influence 405 may correspond to the region of tissue that would be exposed to therapeutically modulating energy based on a defined electrode activation pattern. In the illustrated embodiment, the ablation pattern mapping corresponds to a device that includes five activated electrodes 344 on each strut 340 (FIG. 3B), but the ablation pattern mapping can be used to illustrate the ablation pattern of any number of electrodes 344, any geometry of the electrode layout, and/or any ablation activation protocol (e.g., pulsed activation, multi-polar/sequential activation, etc.).

Referring to FIG. 4A, in some embodiments the ablation pattern may be configured such that each electrode 344 has a region of influence 405 surrounding only the individual electrode 344 (i.e., a "dot" pattern). In other embodiments, the ablation pattern may be such that two or more electrodes 344 may link together to form a sub-grouped regions of influence 405 (FIG. 4B) that define peanut-like or linear shapes between two or more electrodes 344. In further embodiments, the ablation pattern can result in a more expansive or contiguous pattern in which the region of influence 405 extends along multiple electrodes 344 (e.g., along each strut 340 (FIG. 3B)). In still further embodiments, the ablation pattern may result in different regions of influence depending upon the electrode activation pattern, phase angle, target temperature, pulse duration, device structure, and/or other treatment parameters. The three-dimensional views of the ablation patterns (e.g., as shown in FIGS. 4A-4C) can be output to the display 322 (FIG. 3A) and/or other user interfaces to allow the clinician to visualize the changing regions of influence 405 based on different durations of energy application, different electrode activation sequences (e.g., multiplexing), different pulse sequences, different temperature isotherms, and/or other treatment parameters. This information can be used to determine the appropriate ablation algorithm for a patient's specific anatomy (as determined via the system 300 of FIG. 3A). In other embodiments, the three-dimensional visualization of the regions of influence 405 can be used to illustrate the regions from which the electrodes 344 detect data when measuring bioelectrical properties for anatomical mapping. In this embodiment, the three dimensional visualization can be used to determine which electrode activation pattern should be used to determine the desired properties (e.g., impedance, resistance, etc.) in the desired area. In certain embodiments, it may be better to use dot assessments (e.g., FIG. 4A), whereas in other embodiments it may be more appropriate to detect information from linear or larger contiguous regions (e.g., FIGS. 4B and 4C).

Figure 5:
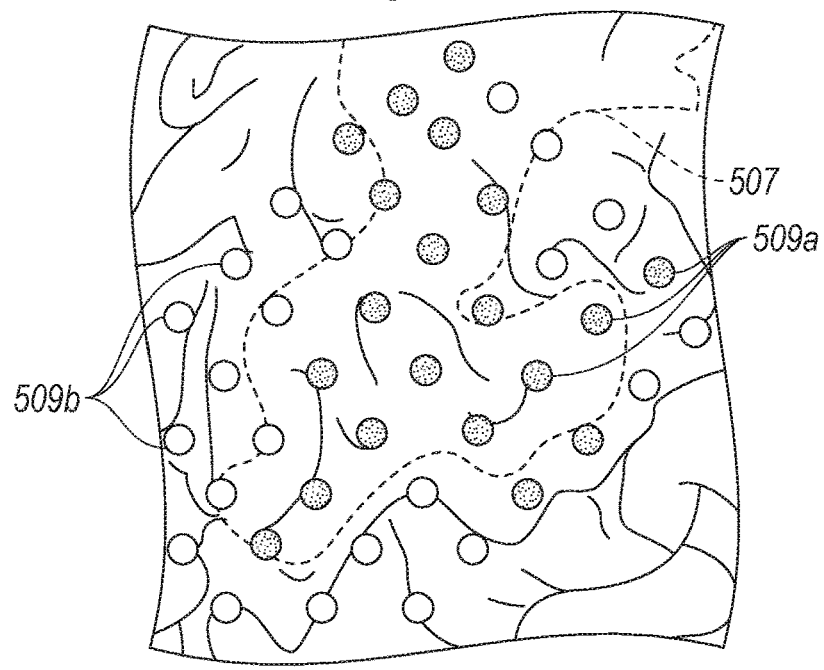
FIG. 5 is an illustration of a projected neuromodulation zone in relation to anatomical structures in a zone of interest in accordance with embodiments of the present technology.

In some embodiments, the mapped ablation pattern is superimposed on the anatomical mapping to identify what structures (e.g., neural structures, vessels, etc.) will be therapeutically modulated or otherwise affected by the therapy. FIG. 5, for example, is an illustration of a predicted or planned neuromodulation zone 507 (shown in broken lines) in relation to previously identified anatomical structures in a zone of interest in accordance with embodiments of the present technology. For example, the illustration shows numerous neural structures 509a-b and, based on the predicted neuromodulation zone 507, identifies which neural structures are expected to be therapeutically modulated. As shown in FIG. 5, the expected therapeutically modulated neural structures 509a are shaded to differentiate them from the non-affected neural structures 509b. In other embodiments, the expected therapeutically modulated neural structures 509a can be differentiated from the non-affected neural structures 509b using different colors and/or other indicators. In further embodiments, the predicted neuromodulation zone 507 and surrounding anatomy (based on anatomical mapping) can be shown in a three dimensional view (e.g., similar to FIGS. 4A-4C) and/or include different visualization features (e.g., color-coding to identify certain anatomical structures, bioelectric properties of the target tissue, etc.). The combined predicted ablation pattern and anatomical mapping (e.g., as shown in FIG. 5) can be output to the display 322 (FIG. 3A) and/or other user interfaces to allow the clinician to select the appropriate ablation algorithm for a patient's specific anatomy.

The imaging provided by the system 300 and shown in FIGS. 4A-6 allows the clinician to visualize the ablation pattern before therapy and adjust the ablation pattern to target specific anatomical structures while avoiding others to prevent collateral effects. For example, the clinician can select a treatment pattern to avoid blood vessels, thereby reducing exposure of the vessel to the therapeutic neuromodulation energy. This reduces the risk of damaging or rupturing vessels and, therefore, prevents immediate or latent bleeding. Further, the selective energy application provided by the neural mapping reduces collateral effects of the therapeutic neuromodulation, such as tissue sloughing off during wound healing (e.g., 1-3 weeks post ablation), thereby reducing the aspiration risk associated with the neuromodulation procedure.

The system 300 can be further configured to apply neuromodulation energy (via the electrodes 344) at specific frequencies attuned to the target neural structure and, therefore, specifically target desired neural structures over non-target structures. For example, the specific neuromodulation frequencies can correspond to the frequencies identified as corresponding to the target structure during neural mapping. As described above, the inherent morphology and composition of the anatomical structures react differently to different frequencies. Thus, frequency-tuned neuromodulation energy tailored to a target structure does not have the same modulating effects on non-target structures. More specifically, applying the neuromodulation energy at the target-specific frequency causes ionic agitation in the target neural structure, leading to differentials in osmotic potentials of the targeted neural structures and dynamic changes in neuronal membronic potentials (resulting from the difference in intra-cellular and extra-cellular fluidic pressure). This causes degeneration, possibly resulting in vacuolar degeneration and, eventually, necrosis at the target neural structure, but is not expected to functionally affect at least some non-target structures (e.g., blood vessels). Accordingly, the system 300 can use the neural-structure specific frequencies to both (1) identify the locations of target neural structures to plan electrode ablation configurations (e.g., electrode geometry and/or activation pattern) that specifically focus the neuromodulation on the target neural structure; and (2) apply the neuromodulation energy at the characteristic neural frequencies to selectively ablate the neural structures responsive to the characteristic neural frequencies. For example, the evaluation/modulation assembly 312 of the system 300 may selectively stimulate and/or modulate parasympathetic fibers, sympathetic fibers, sensory fibers, alpha/beta/delta fibers, C-fibers, anoxic terminals of one or more of the foregoing, insulated over non-insulated fibers (regions with fibers), and/or other neural structures. In some embodiments, the system 300 may also selectively target specific cells or cellular regions during anatomical mapping and/or therapeutic modulation, such as smooth muscle cells, submucosal glands, goblet cells, stratified cellular regions within the nasal mucosa. Therefore, the system 300 provides highly selective neuromodulation therapy specific to targeted neural structures, and reduces the collateral effects of neuromodulation therapy to non-target structures (e.g., blood vessels).

Figure 7:
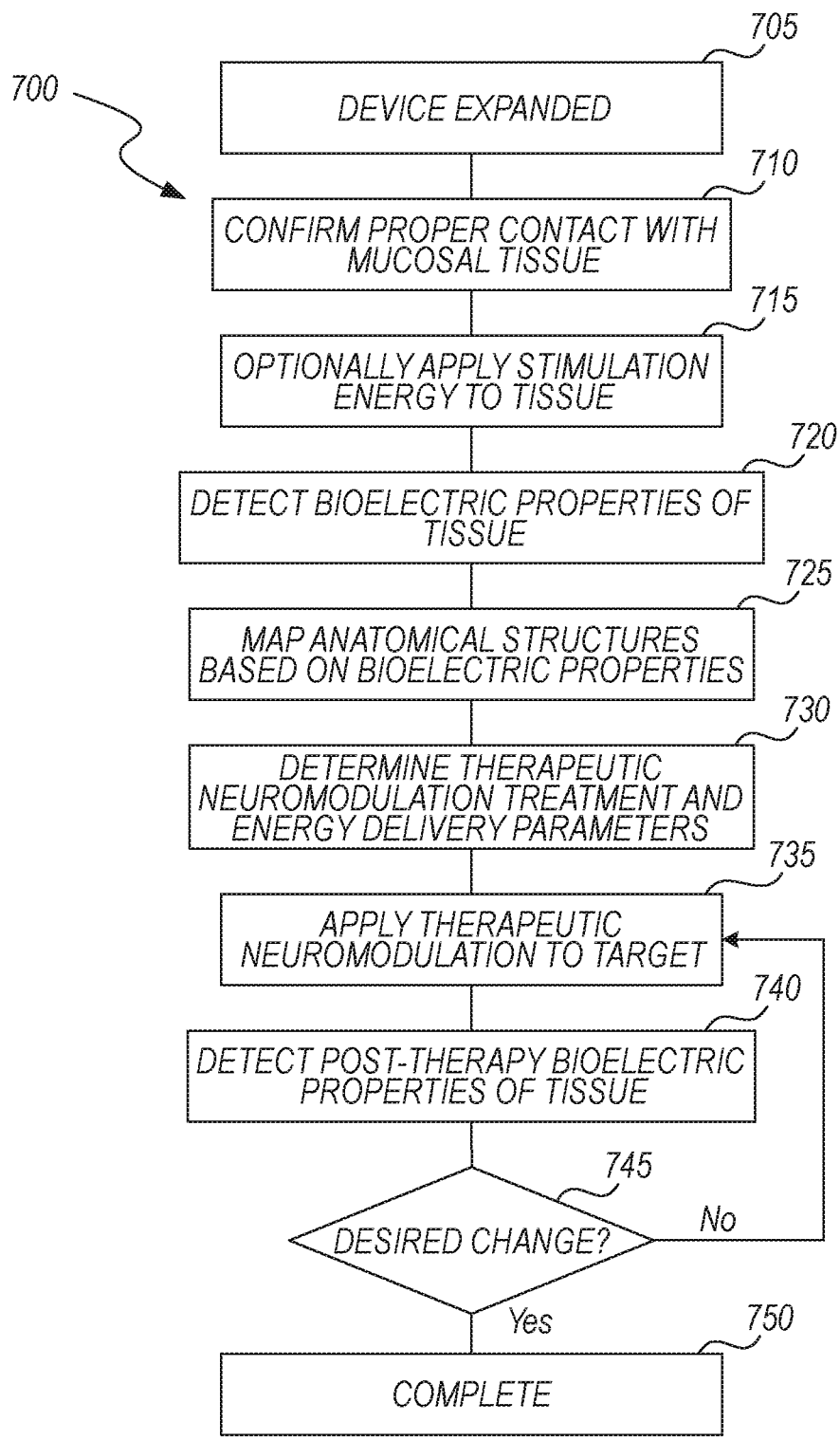
FIG. 7 is a block diagram illustrating a method of anatomical mapping and therapeutic neuromodulation in accordance with embodiments of the present technology.

FIG. 7 is a block diagram illustrating a method 700 of anatomical mapping and therapeutic neuromodulation in accordance with embodiments of the present technology. The method 700 is described below with respect to the system 300 described above with reference to FIGS. 3A-3B, but the method 700 may be implemented using other suitable systems for anatomical evaluation and neuromodulation therapy. As shown in FIG. 7, the method 700 includes expanding an evaluation and modulation device at a zone of interest ("interest zone"), such as in a portion of the nasal cavity (block 705). For example, the evaluation/modulation assembly 312 can be expanded such that at least some of the electrodes 344 are placed in contact with mucosal tissue at the interest zone. The expanded device can then take bioelectric measurements via the electrodes 344 and/or other sensors to ensure that the desired electrodes are in proper contact with the tissue at the interest zone (block 710). In some embodiments, for example, the system 300 detects the impedance and/or resistance across pairs of the electrodes 344 to confirm that the desired electrodes have appropriate surface contact with the tissue and that all of the electrodes are 344 functioning properly.

The method 700 continues by optionally applying an electrical stimulus to the tissue (block 715), and detecting bioelectric properties of the tissue to establish baseline norms of the tissue (block 720). For example, the method 700 can include measuring resistance, complex impedance, current, voltage, nerve firing rate, neuromagnetic field, muscular activation, and/or other parameters that are indicative of the location and/or function of neural structures and/or other anatomical structures (e.g., glandular structures, blood vessels, etc.). In some embodiments, the electrodes 344 send one or more stimulation signals (e.g., pulsed signals or constant signals) to the interest zone to stimulate neural activity and initiate action potentials (block 715). The stimulation signal can have a frequency attuned to a specific target structure (e.g., a specific neural structure, a glandular structure, a vessel) that allows for identification of the location of the specific target structure. The specific frequency of the stimulation signal is a function of the host permeability and, therefore, applying the unique frequency alters the tissue attenuation and the depth into the tissue the RF energy will penetrate. For example, lower frequencies typically penetrate deeper into the tissue than higher frequencies.

Pairs of the non-stimulating electrodes 344 of the evaluation/modulation assembly 312 can then detect one or more bioelectric properties of the tissue that occur in response to the stimulus, such as impedance or resistance. For example, an array of electrodes (e.g., the electrodes 344) can be selectively paired together an a desired pattern (e.g., multiplexing the electrodes 344) to detect the bioelectric properties at desired depths and/or across desired regions to provide a high level of spatial awareness at the interest zone. In certain embodiments, the electrodes 344 can be paired together in a time-sequenced manner according to an algorithm (e.g., provided by the mapping/evaluation/feedback algorithms 320). In various embodiments, stimuli can be injected into the tissue at two or more different frequencies, and the resultant bioelectric responses (e.g., action potentials) in response to each of the injected frequencies can be detected via various pairs of the electrodes 344. For example, an anatomical or neural mapping algorithm can cause the evaluation/modulation assembly 312 to deliver pulsed RF energy at specific frequencies between different pairs of the electrodes 344 and the resultant bioelectric response can be recorded in a time sequenced rotation until the desired interest zone is adequately mapped (i.e., "multiplexing"). For example, the evaluation/modulation assembly 312 can deliver stimulation energy at a first frequency via adjacent pairs of the electrodes 344 for a predetermined time period (e.g., 1-50 milliseconds), and the resultant bioelectric activity (e.g., resistance) can be detected via one or more other pairs of electrodes 344 (e.g., spaced apart from each other to reach varying depths within the tissue). The evaluation/modulation assembly 312 can then apply stimulation energy at a second frequency different from the first frequency, and the resultant bioelectric activity can be detected via the other electrodes. This can continue when the interest zone has been adequately mapped at the desired frequencies. As described in further detail below, in some embodiments the baseline tissue bioelectric properties (e.g., nerve firing rate) are detected using static detection methods (without the injection of a stimulation signal).

After detecting the baseline bioelectric properties, the information can be used to map anatomical structures and/or functions at the interest zone (block 725). For example, the bioelectric properties detected by the electrodes 344 can be amazed via the mapping/evaluation/feedback algorithms 320, and an anatomical map can be output to a user via the display 322. In some embodiments, complex impedance, dielectric, or resistance measurements can be used to map parasympathetic nerves and, optionally, identify neural structures in a diseased state of hyperactivity. The bioelectric properties can also be used to map other non-target structures and the general anatomy, such as blood vessels, bone, and/or glandular structures. The anatomical locations can be provided to a user (e.g., on the display 322) as a two-dimensional map (e.g., illustrating relative intensities as shown in FIG. 6, illustrating specific sites of potential target structures as shown in FIG. 5) and/or as a three-dimensional image. This information can be used to differentiate structures on a submicron, cellular level and identify very specific target structures (e.g., hyperactive parasympathetic nerves). The method 700 can also predict the ablation patterns of the evaluation/modulation assembly 312 based on different electrode neuromodulation protocol (e.g., as shown in FIGS. 4A-4C) and, optionally, superimpose the predicted neuromodulation patterns onto the mapped anatomy to indicate to the user which anatomical structures will be affected by a specific neuromodulation protocol (e.g., as shown in FIG. 5). For example, when the predicted neuromodulation pattern is displayed in relation to the mapped anatomy, a clinician can determine whether target structures will be appropriately ablated and whether non-target structures (e.g., blood vessels) will be undesirably exposed to the therapeutic neuromodulation energy. Thus, the method 700 can be used for planning neuromodulation therapy to locate very specific target structures, avoid non-target structures, and select electrode neuromodulation protocols.

Once the target structure is located and a desired electrode neuromodulation protocol has been selected, the method 700 continues by applying therapeutic neuromodulation to the target structure (block 740). The neuromodulation energy can be applied to the tissue in a highly targeted manner that forms micro-lesions to selectively modulate the target structure, while avoiding non-targeted blood vessels and allowing the surrounding tissue structure to remain healthy for effective wound healing. In some embodiments, the neuromodulation energy can be applied in a pulsed manner, allowing the tissue to cool between modulation pulses to ensure appropriate modulation without undesirably affecting non-target tissue. In some embodiments, the neuromodulation algorithm can deliver pulsed RF energy between different pairs of the electrodes 344 in a time sequenced rotation until neuromodulation is predicted to be complete (i.e., "multi-plexing"). For example, the evaluation/modulation assembly 312 can deliver neuromodulation energy (e.g., having a power of 5-10 W (e.g., 7 W, 8 W, 9 W) and a current of about 50-100 mA) via adjacent pairs of the electrodes 344 until at least one of the following conditions is met: (a) load resistance reaches a predefined maximum resistance (e.g., 350Ω); (b) a thermocouple temperature associated with the electrode pair reaches a predefined maximum temperature (e.g., 80° C.); or (c) a predetermined time period has elapsed (e.g., 10 seconds). After the predetermined conditions are met, the evaluation/modulation assembly 312 can move to the next pair of electrodes in the sequence, and the neuromodulation algorithm can terminate when all of the load resistances of the individual pairs of electrodes is at or above a predetermined threshold (e.g., 300Ω). In various embodiments, the RF energy can be applied at a predetermined frequency (e.g., 450-500 kHz) and is expected to initiate ionic agitation of the specific target structure, while avoiding functional disruption of non-target structures.

During and/or after neuromodulation therapy, the method continues by detecting and, optionally, mapping the post-therapy bioelectric properties of the target site (block 740). This can be performed in a similar manner as described above with respect to blocks 715-725. The post-therapy evaluation can indicate if the target structures (e.g., hyperactive parasympathetic nerves) were adequately modulated or ablated (block 745). If the target structures are not adequately modulated (i.e., if neural activity is still detected in the target structure and/or the neural activity has not decreased), the method 700 can continue by again applying therapeutic neuromodulation to the target (block 735). If the target structures were adequately ablated, the neuromodulation procedure can be completed (block 750).

Selected Embodiments of Detection of Anatomical Structures and Function

Various embodiments of the present technology can include features that measure bioelectric, dielectric, and/or other properties of tissue at target sites to determine the presence, location, and/or activity of neural structures and other anatomical structures and, optionally, map the locations of the detected neural structures and/or other anatomical structures. For example, the present technology can be used to detect glandular structures and, optionally, their mucoserous functions and/or other functions. The present technology can also be configured to detect vascular structures (e.g., arteries) and, optionally, their arterial functions, volumetric pressures, and/or other functions. The mapping features discussed below can be incorporated into any the system 300 (FIGS. 3A and 3B) and/or any other devices disclosed herein to provide an accurate depiction of nerves at the target site.

Neural and/or anatomical detection can occur (a) before the application of a therapeutic neuromodulation energy to determine the presence or location of neural structures and other anatomical structures (e.g., blood vessels, glands, etc.) at the target site and/or record baseline levels of neural activity; (b) during therapeutic neuromodulation to determine the real-time effect of the energy application on the neural fibers at the treatment site; and/or (c) after therapeutic neuromodulation to confirm the efficacy of the treatment on the targeted structures (e.g., nerves glands, etc.). This allows for the identification of very specific anatomical structures (even to the micro-scale or cellular level) and, therefore, provides for highly targeted neuromodulation. This enhances the efficacy and efficiency of the neuromodulation therapy. In addition, the anatomical mapping reduces the collateral effects of neuromodulation therapy to non-target sites. Accordingly, the targeted neuromodulation inhibits damage or rupture of blood vessels (i.e., inhibits undesired bleeding) and collateral damage to tissue that may be of concern during wound healing (e.g., when damage tissue sloughs off of the wall of the nasal wall).

In certain embodiments, the systems disclosed herein can use bioelectric measurements, such as impedance, resistance, voltage, current density, and/or other parameters (e.g., temperature) to determine the anatomy, in particular the neural, glandular, and vascular anatomy, at the target site. The bioelectric properties can be detected after the transmission of a stimulus (e.g., an electrical stimulus, such as RF energy delivered via the electrodes 344 of FIGS. 3A-3B; i.e., "dynamic" detection) and/or without the transmission of a stimulus (i.e., "static" detection).

Dynamic measurements include various embodiments to excite and/or detect primary or secondary effects of neural activation and/or propagation. Such dynamic embodiments involve the heightened states of neural activation and propagation and use this dynamic measurement for nerve location and functional identification relative to the neighboring tissue types. For example, a method of dynamic detection can include: (1) delivering stimulation energy to a treatment site via a treatment device (e.g., the evaluation/modulation assembly 312) to excite parasympathetic nerves at the treatment site; (2) measuring one or more physiological parameters (e.g., resistance, impedance, etc.) at the treatment site via a measuring/sensing array of the treatment device (e.g., the electrodes 344); (4) based on the measurements, identifying the relative presence and position of parasympathetic nerves at the treatment site; and (5) delivering ablation energy to the identified parasympathetic nerves to block the detected para-sympathetic nerves.

Static measurements include various embodiments associated with specific native properties of the stratified or cellular composition at or near the treatment site. The static embodiments are directed to inherent biologic and electrical properties of tissue types at or near the treatment site, the stratified or cellular compositions at or near the treatment site, and contrasting both foregoing measurements with tissue types adjacent the treatment site (and that are not targeted for neuromodulation). This information can be used to localize specific targets (e.g., parasympathetic fibers) and non-targets (e.g., vessels, sensory nerves, etc.). For example, a method of static detection can include: (1) before ablation, utilizing a measuring/sensing array of a treatment device (e.g., the electrodes 344) to determine one or more baseline physiological parameters; (2) geometrically identifying inherent tissue properties within a region of interest based on the measured physiological parameters (e.g., resistance, impedance, etc.); (3) delivering ablation energy to one or more nerves within the region of via treatment device interest; (4) during the delivery of the ablation energy, determining one or more mid-procedure physiological parameters via the measuring/sensing array; and (5) after the delivery of ablation energy, determining one or more post-procedure physiological parameters via the measurement/sensing array to determine the effectiveness of the delivery of the ablation energy on blocking the nerves that received the ablation energy.

After the initial static and/or dynamic detection of bioelectric properties, the location of anatomical features can be used to determine where the treatment site(s) should be with respect to various anatomical structures for therapeutically effective neuromodulation of the targeted parasympathetic nasal nerves. The bioelectric and other physiological properties discussed herein can be detected via electrodes (e.g., the electrodes 344 of the evaluation/modulation assembly 312 of FIGS. 3A and 3B), and the electrode pairings on a device (e.g., evaluation/modulation assembly 312) can be selected to obtain the bioelectric data at specific zones or regions and at specific depths of the targeted regions. The specific properties detected at or surrounding target neuromodulation sites and associated methods for obtaining these properties are described below. These specific detection and mapping methods discussed below are described with reference to the system 300 of FIGS. 3A and 3B, although the methods can be implemented on other suitable systems and devices that provide for anatomical identification, anatomical mapping and/or neuromodulation therapy.

Neural Identification and Mapping

In many neuromodulation procedures, it is beneficial to identify the portions of the nerves that fall within a zone and/or region of influence (referred to as the "interest zone") of the energy delivered by a neuromodulation device 302 (FIG. 3A), as well as the relative three-dimensional position of the neural structures relative to the neuromodulation device 302. Characterizing the portions of the neural structures within the interest zone and/or determining the relative positions of the neural structures within the interest zone enables the clinician to (1) selectively activate target neural structures over non-target structures (e.g., blood vessels), and (2) sub-select specific targeted neural structures (e.g., parasympathetic nerves) over non-target neural structures (e.g., sensory nerves, subgroups of neural structures, neural structures having certain compositions or morphologies). The target structures (e.g., parasympathetic nerves) and non-target structures (e.g., blood vessels, sensory nerves, etc.) can be identified based on the inherent signatures of specific structures, which are defined by the unique morphological compositions of the structures and the bioelectrical properties associated with these morphological compositions. For example, unique, discrete frequencies can be associated with morphological compositions and, therefore, be used to identify certain structures. The target and non-target structures can also be identified based on relative bioelectrical activation of the structures to sub-select specific neuronal structures. Further, target and non-target structures can be identified by the differing detected responses of the structures to a tailored injected stimuli. For example, the systems described herein can detect the magnitude of response of structures and the difference in the responses of anatomical structures with respect to differing stimuli (e.g., stimuli injected at different frequencies).

At least for purposes of this disclosure, a nerve can include the following portions that are defined based on their respective orientations relative to the interest zone: terminating neural structures (e.g., terminating axonal structures), branching neural structures (e.g., branching axonal structures), and travelling neural structures (e.g., travelling axonal structures). For example, terminating neural structures enter the zone but do not exit. As such, terminating neural structures are terminal points for neuronal signaling and activation. Branching neural structures are nerves that enter the interest zone and increase number of nerves exiting the interest zone. Branching neural structures are typically associated with a reduction in relative geometry of nerve bundle. Travelling neural structures are nerves that enter the interest zone and exit the zone with no substantially no change in geometry or numerical value.

The system 300 can be used to detect voltage, current, complex impedance, resistance, permittivity, and/or conductivity, which are tied to the compound action potentials of nerves, to determine and/or map the relative positions and proportionalities of nerves in the interest zone. Neuronal cross-sectional area ("CSA") is expected to be due to the increase in axonic structures. Each axon is a standard size. Larger nerves (in cross-sectional dimension) have a larger number of axons than nerves having smaller cross-sectional dimensions. The compound action responses from the larger nerves, in both static and dynamic assessments, are greater than smaller nerves. This is at least in part because the compound action potential is the cumulative action response from each of the axons. When using static analysis, for example, the system 300 can directly measure and map impedance or resistance of nerves and, based on the determined impedance or resistance, determine the location of nerves and/or relative size of the nerves. In dynamic analysis, the system 300 can be used to apply a stimulus to the interest zone and detect the dynamic response of the neural structures to the stimulus. Using this information, the system 300 can determine and/or map impedance or resistance in the interest zone to provide information related to the neural positions or relative nerve sizes. Neural impedance mapping can be illustrated by showing the varying complex impedance levels at a specific location at differing cross-sectional depths (e.g., as shown in FIG. 6). In other embodiments, neural impedance or resistance can be mapped in a three-dimensional display.

Identifying the portions and/or relative positions of the nerves within the interest zone can inform and/or guide selection of one or more treatment parameters (e.g., electrode ablation patterns, electrode activation plans, etc.) of the system 300 for improving treatment efficiency and efficacy. For example, during neural monitoring and mapping, the system 300 can identify the directionality of the nerves based at least in part on the length of the neural structure extending along the interest zone, relative sizing of the neural structures, and/or the direction of the action potentials. This information can then be used by the system 300 or the clinician to automatically or manually adjust treatment parameters (e.g., selective electrode activation, bipolar and/or multipolar activation, and/or electrode positioning) to target specific nerves or regions of nerves. For example, the system 300 can selectively activate specific electrodes 344, electrode combinations (e.g., asymmetric or symmetric), and/or adjust the bi-polar or multi-polar electrode configuration. In some embodiments, the system 300 can adjust or select the waveform, phase angle, and/or other energy delivery parameters based on the nerve portion/position mapping and/or the nerve proportionality mapping. In some embodiments, structure and/or properties of the electrodes 344 themselves (e.g., material, surface roughening, coatings, cross-sectional area, perimeter, penetrating, penetration depth, surface-mounted, etc.) may be selected based on the nerve portion and proportionality mapping.

In various embodiments, treatment parameters and/or energy delivery parameters can be adjusted to target on-axis or near axis travelling neural structures and/or avoid the activation of traveling neural structures that are at least generally perpendicular to the evaluation/modulation assembly 312. Greater portions of the on-axis or near axis travelling neural structures are exposed and susceptible to the neuromodulation energy provided by the evaluation/modulation assembly 312 than a perpendicular travelling neural structure, which may only be exposed to therapeutic energy at a discrete cross-section. Therefore, the evaluation/modulation assembly 312 is more likely to have a greater effect on the on-axis or near axis travelling neural structures. The identification of the neural structure positions (e.g., via complex impedance or resistance mapping) can also allow targeted energy delivery to travelling neural structures rather than branching neural structures (typically downstream of the travelling neural structures) because the travelling neural structures are closer to the nerve origin and, therefore, more of the nerve is affected by therapeutic neuromodulation, thereby resulting in a more efficient treatment and/or a higher efficacy of treatment. Similarly, the identification of neural structure positions can be used to target travelling and branching neural structures over terminal neural structures. In some embodiments, the treatment parameters can be adjusted based on the detected neural positions to provide a selective regional effect. For example, a clinician can target downstream portions of the neural structures if only wanting to influence partial effects on very specific anatomical structures or positions.

In various embodiments, neural locations and/or relative positions of nerves can be determined by detecting the nerve-firing voltage and/or current over time. An array of the electrodes 344 can be positioned in contact with tissue at the interest zone, and the electrodes 344 can measure the voltage and/or current associated with nerve-firing. This information can optionally be mapped (e.g., on a display 322) to identify the location of nerves in a hyper state (i.e., excessive parasympathetic tone). Rhinitis is at least in part the result of over-firing nerves because this hyper state drives the hyper-mucosal production and hyper-mucosal secretion. Therefore, detection of nerve firing rate via voltage and current measurements can be used to locate the portions of the interest region that include hyper-parasympathetic neural function (i.e., nerves in the diseased state). This allows the clinician to locate specific nerves (i.e., nerves with excessive parasympathetic tone) before neuromodulation therapy, rather than simply targeting all parasympathetic nerves (including non-diseased state parasympathetic nerves) to ensure that the correct tissue is treated during neuromodulation therapy. Further, nerve firing rate can be detected during or after neuromodulation therapy so that the clinician can monitor changes in nerve firing rate to validate treatment efficacy. For example, recording decreases or elimination of nerve firing rate after neuromodulation therapy can indicate that the therapy was effective in therapeutically treating the hyper/diseased nerves.

In various embodiments, the system 300 can detect neural activity using dynamic activation by injecting a stimulus signal (i.e., a signal that temporarily activates nerves) via one or more of the electrodes 344 to induce an action potential, and other pairs of electrodes 344 can detect bioelectric properties of the neural response. Detecting neural structures using dynamic activation involves detecting the locations of action potentials within the interest zone by measuring the discharge rate in neurons and the associated processes. The ability to numerically measure, profile, map, and/or image fast neuronal depolarization for generating an accurate index of activity is a factor in measuring the rate of discharge in neurons and their processes. The action potential causes a rapid increase in the voltage across nerve fiber and the electrical impulse then spreads along the fiber. As an action potential occurs, the conductance of a neural cell membrane changes, becoming about 40 times larger than it is when the cell is at rest. During the action potential or neuronal depolarization, the membrane resistance diminishes by about 80 times, thereby allowing an applied current to enter the intracellular space as well. Over a population of neurons, this leads to a net decrease in the resistance during coherent neuronal activity, such as chronic para-sympathetic responses, as the intracellular space will provide additional conductive ions. The magnitude of such fast changes has been estimated to have local resistivity changes with recording near DC is 2.8-3.7% for peripheral nerve bundles (e.g., including the nerves in the nasal cavity).

Detecting neural structures using dynamic activation includes detecting the locations of action potentials within the interest zone by measuring the discharge rate in neurons and the associated processes. The basis of each this discharge is the action potential, during which there is a depolarization of the neuronal membrane of up to 110 mV or more, lasting approximately 2 milliseconds, and due to the transfer of micromolar quantities of ions (e.g., sodium and potassium) across the cellular membrane. The complex impedance or resistance change due to the neuronal membrane falls from 1000 to 25 Ωcm. The introduction of a stimulus and subsequent measurement of the neural response can attenuate noise and improve signal to noise ratios to precisely focus on the response region to improve neural detection, measurement, and mapping.

In some embodiments, the difference in measurements of physiological parameters (e.g., complex impedance, resistance, voltage) over time, which can reduce errors, can be used to create a neural profiles, spectrums, or maps. For example, the sensitivity of the system 300 can be improved because this process provides repeated averaging to a stimulus. As a result, the mapping function outputs can be a unit-less ratio between the reference and test collated data at a single frequency and/or multiple frequencies and/or multiple amplitudes. Additional considerations may include multiple frequency evaluation methods that consequently expand the parameter assessments, such as resistivity, admittivity, center frequency, or ratio of extra- to intracellular resistivity.

In some embodiments, the system 300 may also be configured to indirectly measure the electrical activity of neural structures to quantify the metabolic recovery processes that accompany action potential activity and act to restore ionic gradients to normal. These are related to an accumulation of ions in the extracellular space. The indirect measurement of electrical activity can be approximately a thousand times larger (in the order of millimolar), and thus are easier to measure and can enhance the accuracy of the measured electrical properties used to generate the neural maps.

The system 300 can perform dynamic neural detection by detecting nerve-firing voltage and/or current and, optionally, nerve firing rate over time, in response to an external stimulation of the nerves. For example, an array of the electrodes 344 can be positioned in contact with tissue at the interest zone, one or more of the electrodes 344 can be activated to inject a signal into the tissue that stimulates the nerves, and other electrodes 344 of the electrode array can measure the neural voltage and/or current due to nerve firing in response to the stimulus. This information can optionally be mapped (e.g., on a display 322) to identify the location of nerves and, in certain embodiments, identify parasympathetic nerves in a hyper state (e.g., indicative of Rhinitis or other diseased state). The dynamic detection of neural activity (voltage, current, firing rate, etc.) can be performed before neuromodulation therapy to detect target nerve locations to select the target site and treatment parameters to ensure that the correct tissue is treated during neuromodulation therapy. Further, dynamic detection of neural activity can be performed during or after neuromodulation therapy to allow the clinician to monitor changes in neural activity to validate treatment efficacy. For example, recording decreases or elimination of neural activity after neuromodulation therapy can indicate that the therapy was effective in therapeutically treating the hyper/diseased nerves.

As described in further detail below with respect to FIG. 9, in some embodiments a stimulating signal can be delivered to the vicinity of the targeted nerve via one or more penetrating electrodes (e.g., microneedles that penetrate tissue) associated with the evaluation/modulation assembly 312 and/or a separate device. The stimulating signal generates an action potential, which causes smooth muscle cells or other cells to contract. The location and strength of this contraction can be detected via the penetrating electrode(s) and, thereby, indicate to the clinician the distance to the nerve and/or the location of the nerve relative to the stimulating needle electrode. In some embodiments, the stimulating electrical signal may have a voltage of typically 1-2 mA or greater and a pulse width of typically 100-200 microseconds or greater. Shorter pulses of stimulation result in better discrimination of the detected contraction, but may require more current. The greater the distance between the electrode and the targeted nerve, the more energy is required to stimulate. The stimulation and detection of contraction strength and/or location enables identification of how close or far the electrodes are from the nerve, and therefore can be used to localize the nerve spatially. In some embodiments, varying pulse widths may be used to measure the distance to the nerve. As the needle becomes closer to the nerve, the pulse duration required to elicit a response becomes less and less.

To localize nerves via muscle contraction detection, the system 300 can vary pulse-width or amplitude to vary the energy (Energy=pulse-width*amplitude) of the stimulus delivered to the tissue via the penetrating electrode(s). By varying the stimulus energy and monitoring muscle contraction via the penetrating electrodes and/or other type of sensor, the system 300 can estimate the distance to the nerve. If a large amount of energy is required to stimulate the nerve/contract the muscle, the stimulating/penetrating electrode is far from the nerve. As the stimulating/penetrating electrode, moves closer to the nerve, the amount of energy required to induce muscle contraction will drop. For example, an array of penetrating electrodes can be positioned in the tissue at the interest zone and one or more of the electrodes can be activated to apply stimulus at different energy levels until they induce muscle contraction. Using an iterative process, localize the nerve (e.g., via the mapping/evaluation/feedback algorithm 320).

In some embodiments, the system 300 can measure the muscular activation from the nerve stimulus (e.g., via the electrodes 344) to determine neural positioning for neural mapping, without the use of penetrating electrodes. In this embodiment, the treatment device targets the smooth muscle cells' varicosities surrounding the submucosal glands and the vascular supply, and then the compound muscle action potential. This can be used to summate voltage response from the individual muscle fiber action potentials. The shortest latency is the time from stimulus artifact to onset of the response. The corresponding amplitude is measured from baseline to negative peak and measured in millivolts (mV). Nerve latencies (mean±SD) in adults typically range about 2-6 milliseconds, and more typically from about 3.4±0.8 to about 4.0±0.5 milliseconds. A comparative assessment may then be made which compares the outputs at each time interval (especially pre- and post-energy delivery) in addition to a group evaluation using the alternative nasal cavity. This is expected to provide an accurate assessment of the absolute value of the performance of the neural functioning because muscular action/activation may be used to infer neural action/activation and muscle action/activation is a secondary effect or by-product whilst the neural function is the absolute performance measure.

In some embodiments, the system 300 can record a neuromagnetic field outside of the nerves to determine the internal current of the nerves without physical disruption of the nerve membrane. Without being bound by theory, the contribution to the magnetic field from the current inside the membrane is two orders of magnitude larger than that from the external current, and that the contribution from current within the membrane is substantially negligible. Electrical stimulation of the nerve in tandem with measurements of the magnetic compound action fields ("CAFs") can yield sequential positions of the current dipoles such that the location of the conduction change can be estimated (e.g., via the least-squares method). Visual representation (e.g., via the display 322) using magnetic contour maps can show normal or non-normal neural characteristics (e.g., normal can be equated with a characteristic quadrupolar pattern propagating along the nerve), and therefore indicate which nerves are in a diseases, hyperactive state and suitable targets for neuromodulation.

During magnetic field detection, an array of the electrodes 344 can be positioned in contact with tissue at the interest zone and, optionally, one or more of the electrodes 344 can be activated to inject an electrical stimulus into the tissue. As the nerves in the interest zone fire (either in response to a stimulus or in the absence of it), the nerve generates a magnetic field (e.g., similar to a current carrying wire), and therefore changing magnetic fields are indicative of the nerve nerve-firing rate. The changing magnetic field caused by neural firing can induce a current detected by nearby sensor wire (e.g., the sensor 314) and/or wires associated with the nearby electrodes 344. By measuring this current, the magnetic field strength can be determined. The magnetic fields can optionally be mapped (e.g., on a display 322) to identify the location of nerves and select target nerves (nerves with excessive parasympathetic tone) before neuromodulation therapy to ensure that the desired nerves are treated during neuromodulation therapy. Further, the magnetic field information can be used during or after neuromodulation therapy so that the clinician can monitor changes in nerve firing rate to validate treatment efficacy.

In other embodiments, the neuromagnetic field is measured with a Hall Probe or other suitable device, which can be integrated into the evaluation/modulation assembly 312 and/or part of a separate device delivered to the interest zone. Alternatively, rather than measuring the voltage in the second wire, the changing magnetic field can be measured in the original wire (i.e. the nerve) using a Hall probe. A current going through the Hall probe will be deflected in the semi-conductor. This will cause a voltage difference between the top and bottom portions, which can be measured. In some aspects of this embodiments, three orthogonal planes are utilized.

In some embodiments, the system 300 can be used to induce electromotive force ("EMF") in a wire (i.e., a frequency-selective circuit, such as a tunable/LC circuit) that is tunable to resonant frequency of a nerve. In this embodiment, the nerve can be considered to be a current carrying wire, and the firing action potential is a changing voltage. This causes a changing current which, in turn, causes a changing magnetic flux (i.e., the magnetic field that is perpendicular to the wire). Under Faraday's Law of Induction/Faraday's Principle, the changing magnetic flux induces EMF (including a changing voltage) in a nearby sensor wire (e.g., integrated into the evaluation/modulation assembly 312, the sensor 314, and/or other structure), and the changing voltage can be measured via the system 300.

In further embodiments, the sensor wire (e.g., the sensor 314) is an inductor and, therefore, provides an increase of the magnetic linkage between the nerve (i.e., first wire) and the sensor wire (i.e., second wire), with more turns for increasing effect. (e.g., V2, rms=V1, rms (N2/N1)). Due to the changing magnetic field, a voltage is induced in the sensor wire, and this voltage can be measured and used to estimate current changes in the nerve. Certain materials can be selected to enhance the efficiency of the EMF detection. For example, the sensor wire can include a soft iron core or other high permeability material for the inductor.

During induced EMF detection, the evaluation/modulation assembly 312 and/or other device including a sensor wire is positioned in contact with tissue at the interest zone and, optionally, one or more of the electrodes 344 can be activated to inject an electrical stimulus into the tissue. As the nerves in the interest zone fire (either in response to a stimulus or in the absence of it), the nerve generates a magnetic field (e.g., similar to a current carrying wire) that induces a current in the sensor wire (e.g., the sensor 314). This information can be used to determine neural location and/or map the nerves (e.g., on a display 322) to identify the location of nerves and select target nerves (nerves with excessive parasympathetic tone) before neuromodulation therapy to ensure that the desired nerves are treated during neuromodulation therapy. EMF information can also be used during or after neuromodulation therapy so that the clinician can monitor changes in nerve firing rate to validate treatment efficacy.

In some embodiments, the system 300 can detect magnetic fields and/or EMF generated at a selected frequency that corresponds to a particular type of nerve. The frequency and, by extension, the associated nerve type of the detected signal can be selected based on an external resonant circuit. Resonance occurs on the external circuit when it is matched to the frequency of the magnetic field of the particular nerve type and that nerve is firing. In manner, the system 300 can be used to locate a particular sub-group/type of nerves.

In some embodiments, the system 300 can include a variable capacitor frequency-selective circuit to identify the location and/or map specific nerves (e.g., parasympathetic nerve, sensory nerve, nerve fiber type, nerve subgroup, etc.). The variable capacitor frequency-selective circuit can be defined by the sensor 314 and/or other feature of the evaluation/modulation assembly 312. Nerves have different resonant frequencies based on their function and structure. Accordingly, the system 300 can include a tunable LC circuit with a variable capacitor (C) and/or variable inductor (L) that can be selectively tuned to the resonant frequency of desired nerve types. This allows for the detection of neural activity only associated with the selected nerve type and its associated resonant frequency. Tuning can be achieved by moving the core in and out of the inductor. For example, tunable LC circuits can tune the inductor by: (i) changing the number of coils around the core; (ii) changing the cross-sectional area of the coils around the core; (iii) changing the length of the coil; and/or (iv) changing the permeability of the core material (e.g., changing from air to a core material). Systems including such a tunable LC circuit provide a high degree of dissemination and differentiation not only as to the activation of a nerve signal, but also with respect to the nerve type that is activated and the frequency at which the nerve is firing.

Anatomical Mapping

In various embodiments, the system 300 is further configured to provide minimally-invasive anatomical mapping that uses focused energy current/voltage stimuli from a spatially localized source (e.g., the electrodes 344) to cause a change in the conductivity of the of the tissue at the interest zone and detect resultant biopotential and/or bioelectrical measurements (e.g., via the electrodes 344). The current density in the tissue changes in response to changes of voltage applied by the electrodes 344, which creates a change in the electric current that can be measured with the evaluation/modulation assembly 312 and/or other portions of the system 300. The results of the bioelectrical and/or biopotential measurements can be used to predict or estimate relative absorption profilometry to predict or estimate the tissue structures in the interest zone. More specifically, each cellular construct has unique conductivity and absorption profiles that can be indicative of a type of tissue or structure, such as bone, soft tissue, vessels, nerves, types of nerves, and/or certain neural structures. For example, different frequencies decay differently through different types of tissue. Accordingly, by detecting the absorption current in a region, the system 300 can determine the underlying structure and, in some instances, to a sub-microscale, cellular level that allows for highly specialized target localization and mapping. This highly specific target identification and mapping enhances the efficacy and efficiency of neuromodulation therapy, while also enhancing the safety profile of the system 300 to reduce collateral effects on non-target structures.

To detect electrical and dielectric tissue properties (e.g., resistance, complex impedance, conductivity, and/or, permittivity as a function of frequency), the electrodes 344 and/or another electrode array is placed on tissue at an interest region, and an internal or external source (e.g., the generator 316) applies stimuli (current/voltage) to the tissue. The electrical properties of the tissue between the source and the receiver electrodes 344 are measured, as well as the current and/or voltage at the individual receiver electrodes 344. These individual measurements can then be converted into an electrical map/image/profile of the tissue and visualized for the user on the display 322 to identify anatomical features of interest and, in certain embodiments, the location of firing nerves. For example, the anatomical mapping can be provided as a color-coded or gray-scale three-dimensional or two-dimensional map showing differing intensities of certain bioelectric properties (e.g., resistance, impedance, etc.), or the information can be processed to map the actual anatomical structures for the clinician. This information can also be used during neuromodulation therapy to monitor treatment progression with respect to the anatomy, and after neuromodulation therapy to validate successful treatment. In addition, the anatomical mapping provided by the bioelectrical and/or biopotential measurements can be used to track the changes to non-target tissue (e.g., vessels) due to neuromodulation therapy to avoid negative collateral effects. For example, a clinician can identify when the therapy begins to ligate a vessel and/or damage tissue, and modify the therapy to avoid bleeding, detrimental tissue ablation, and/or other negative collateral effects.

Furthermore, the threshold frequency of electric current used to identify specific targets can subsequently be used when applying therapeutic neuromodulation energy. For example, the neuromodulation energy can be applied at the specific threshold frequencies of electric current that are target neuronal-specific and differentiated from other non-targets (e.g., blood vessels, non-target nerves, etc.). Applying ablation energy at the target-specific frequency results in an electric field that creates ionic agitation in the target neural structure, which leads to differentials in osmotic potentials of the targeted neural structures. These osmotic potential differentials cause dynamic changes in neuronal membronic potentials (resulting from the difference in intracellular and extra-cellular fluidic pressure) that lead to vacuolar degeneration of the targeted neural structures and, eventually, necrosis. Using the highly targeted threshold neuromodulation energy to initiate the degeneration allows the system 300 to delivery therapeutic neuromodulation to the specific target, while surrounding blood vessels and other non-target structures are functionally maintained.

In some embodiments, the system 300 can further be configured to detect bioelectrical properties of tissue by non-invasively recording resistance changes during neuronal depolarization to map neural activity with electrical impedance, resistance, bio-impedance, conductivity, permittivity, and/or other bioelectrical measurements. Without being bound by theory, when a nerve depolarizes, the cell membrane resistance decreases (e.g., by approximately 80×) so that current will pass through open ion channels and into the intracellular space. Otherwise the current remains in the extracellular space. For non-invasive resistance measurements, tissue can be stimulated by applying a current of less than 100 Hz, such as applying a constant current square wave at 1 Hz with an amplitude less than 25% (e.g., 10%) of the threshold for stimulating neuronal activity, and thereby preventing or reducing the likelihood that the current does not cross into the intracellular space or stimulating at 2 Hz. In either case, the resistance and/or complex impedance is recorded by recording the voltage changes. A complex impedance or resistance map or profile of the area can then be generated (e.g., as shown in FIG. 6).

For impedance/conductivity/permittivity detection, the electrodes 344 and/or another electrode array are placed on tissue at an interest region, and an internal or external source (e.g., the generator 316) applies stimuli to the tissue, and the current and/or voltage at the individual receiver electrodes 344 is measured. The stimuli can be applied at different frequencies to isolate different types of nerves. These individual measurements can then be converted into an electrical map/image/profile of the tissue and visualized for the user on the display 322 to identify anatomical features of interest. The neural mapping can also be used during neuromodulation therapy to select specific nerves for therapy, monitor treatment progression with respect to the nerves and other anatomy, and validate successful treatment.

In some embodiments of the neural and/or anatomical detection methods described above, the procedure can include comparing the mid-procedure physiological parameter(s) to the baseline physiological parameter(s) and/or other, previously-acquired mid-procedure physiological parameter(s) (within the same energy delivery phase). Such a comparison can be used to analyze state changes in the treated tissue. The mid-procedure physiological parameter(s) may also be compared to one or more predetermined thresholds, for example, to indicate when to stop delivering treatment energy. In some embodiments of the present technology, the measured baseline, mid-, and post-procedure parameters include a complex impedance. In some embodiments of the present technology, the post-procedure physiological parameters are measured after a pre-determined time period to allow the dissipation of the electric field effects (ionic agitation and/or thermal thresholds), thus facilitating accurate assessment of the treatment.

In some embodiments, the anatomical mapping methods described above can be used to differentiate the depth of soft tissues within the nasal mucosa. The depth of mucosa on the turbinates is great whilst the depth off the turbinate is shallow and, therefore, identifying the tissue depth in the present technology also identifies positions within the nasal mucosa and where precisely to target. Further, by providing the micro-scale spatial impedance mapping of epithelial tissues as described above, the inherent unique signatures of stratified layers or cellular bodies can be used as identifying the region of interest. For example, different regions have larger or small populations of specific structures, such as submucosal glands, so target regions can be identified via the identification of these structures.

In some embodiments, the system 300 includes additional features that can be used to detect anatomical structures and map anatomical features. For example, the system 300 can include an ultrasound probe for identification of neural structures and/or other anatomical structures. Higher frequency ultrasound provides higher resolution, but less depth of penetration. Accordingly, the frequency can be varied to achieve the appropriate depth and resolution for neural/anatomical localization. Functional identification may rely on the spatial pulse length ("SPL") (wavelength multiplied by number of cycles in a pulse). Axial resolution (SPL/2) may also be determined to locate nerves.

In some embodiments, the system 300 can further be configured to emit stimuli with selective parameters that suppress rather than fully stimulate neural activity. for example, in embodiments where the strength-duration relationship for extracellular neural stimulation is selected and controlled, a state exists where the extracellular current can hyperpolarize cells, resulting in suppression rather than stimulation spiking behavior (i.e., a full action potential is not achieved). Both models of ion channels, HH and RGC, suggest that it is possible to hyperpolarize cells with appropriately designed burst extracellular stimuli, rather than extending the stimuli. This phenomenon could be used to suppress rather than stimulate neural activity during any of the embodiments of neural detection and/or modulation described herein.

Selected Embodiments of Evaluation and Neuromodulation Devices

Figure 8A:
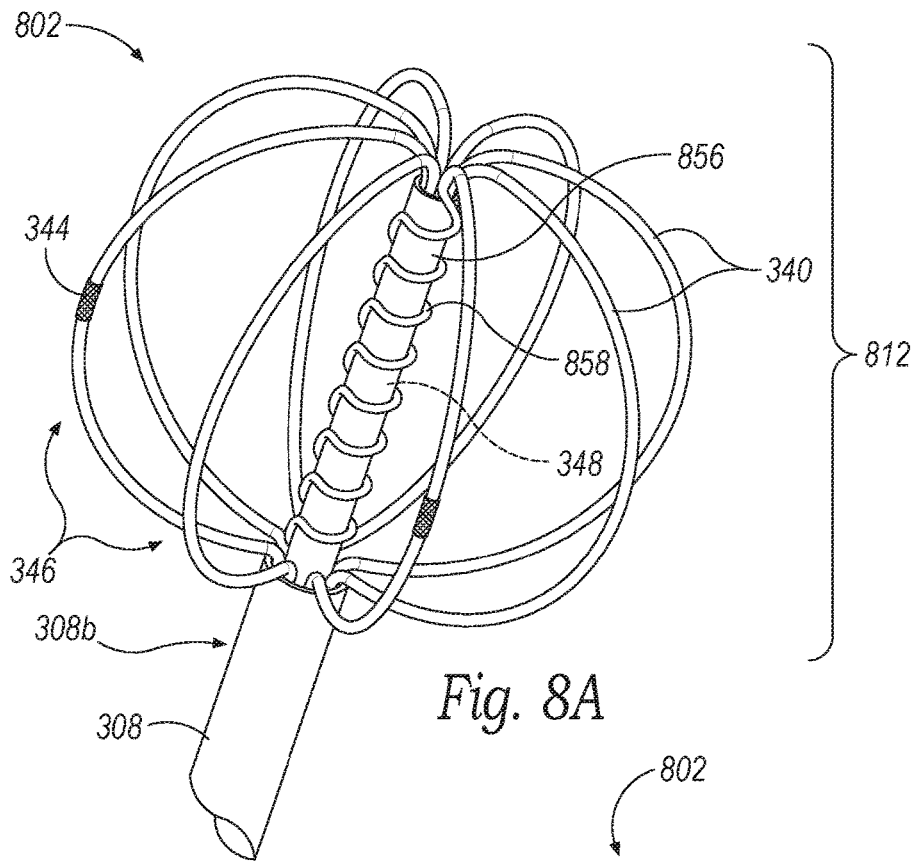
FIGS. 8A and 8B are enlarged isometric views of a distal portion of a neuromodulation and mapping device configured in accordance with some embodiments of the present technology.
Figure 8B:
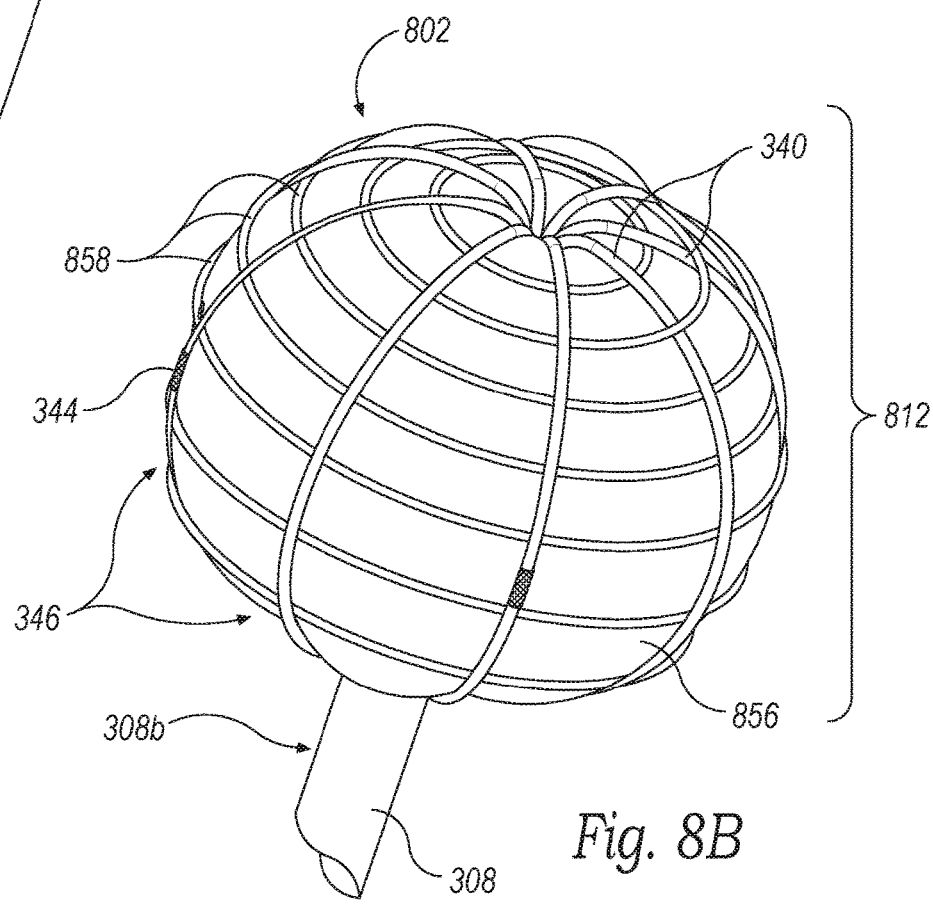

FIGS. 8A and 8B are isometric views of a distal portion of a neuromodulation and mapping device 802 ("device 802") configured in accordance with an embodiment of the present technology. The device 802 can include various features generally similar to the features of the device 302 described above with reference to FIGS. 3A and 3B. For example, the device 802 includes an evaluation/modulation assembly 812 at the distal portion 308b of the shaft 308. The evaluation/modulation 812 includes a plurality of struts 340 that form branches 346 and define an expandable frame or basket 342, and optionally include one or more electrodes 344 disposed on one or more of the struts 340. As shown in FIGS. 8A and 8B, the device 802 can further include an expandable member 856 (e.g., a balloon) carried by the support member 348 and expandable within the basket 342. The expandable member 856 can include one or more electrodes 858 that extend in a circumferential pattern across the outer surface of the expandable member 856. For example, the one or more electrodes 858 can define a coil shape disposed on the expandable member 856. The electrodes 858 can be used for detection of bioelectric features (e.g., complex impedance, resistance, etc.) to allow for mapping of the anatomy at the interest zone before, during, and/or after therapeutic neuromodulation via the other electrodes 344. In other embodiments, the electrodes 858 can be configured to apply energy for therapeutic neuromodulation.

As shown in FIG. 8B, the electrode(s) 858 can be positioned across a substantial portion of the expandable member 856 that proves an expansive area at which impedance and/or other properties can be detected across the tissue and, therefore, may provide a more detailed mapping of the tissue and nerves at the treatment site. The expandable member 856 can also closely conform to the adjacent tissue at the zone of interest and, therefore, facilitate contact between the electrode(s) 858 and the tissue. In other embodiments, the electrodes 858 can have different configurations on the outer surface of the expandable member 856. When there are multiple electrodes 358, the individual electrodes 858 can be selectively activated at a specific polarity, and therefore the electrode array can be configured in a variety of static configurations and a dynamically change sequences (e.g., sesquipolar application of current) that may be advantageous for mapping functions.

In operation, the expandable member 856 can be inflated or otherwise expanded (FIG. 8B) to place at least a portion of the electrodes 858 into contact with tissue at the target site. The electrodes 858 can measure various bioelectric properties of the tissue (e.g., impedance, action potentials, etc.) to detect, locate, and/or map the neural structures and/or other anatomical structures at the interest zone. In certain embodiments, the electrodes 344 on the struts 340 and/or a portion of the electrodes 858 on the expandable member 856 can apply a stimulating pulse of RF energy, and the electrodes 858 can detect the resultant neural response. After mapping, the expandable member 856 can be deflated or collapsed (FIG. 8A), and the electrodes 344 on the struts 340 can apply therapeutically effective neuromodulation energy to the target site. For example, the ablation pattern of the electrodes 344 can be based on the neural locations identified via the information detected from the sensing electrodes 858 on the expandable member 856. In other embodiments, the expandable member 856 may remain expanded during neuromodulation, and the electrodes 858 can detect neural activity during the neuromodulation procedure or the electrodes 858 can themselves be configured to apply neuromodulation energy to the treatment site. After applying the neuromodulation energy, the electrodes 858 on the expandable member 856 can again be placed into contact with tissue at the target site, and used to record bioelectric properties (e.g., impedance, resistance, voltage, etc.). The detected properties taken before, during, and/or after neuromodulation can be compared to each other to determine whether the neuromodulation was therapeutically effective. If not, the electrodes 344 can again apply therapeutic neuromodulation energy to the same treatment site, or the configuration of the active electrodes 344 can be changed to apply therapeutic neuromodulation energy in a different pattern or sequence, and/or the evaluation/modulation assembly 812 can be moved to a different treatment site.

Figure 9:
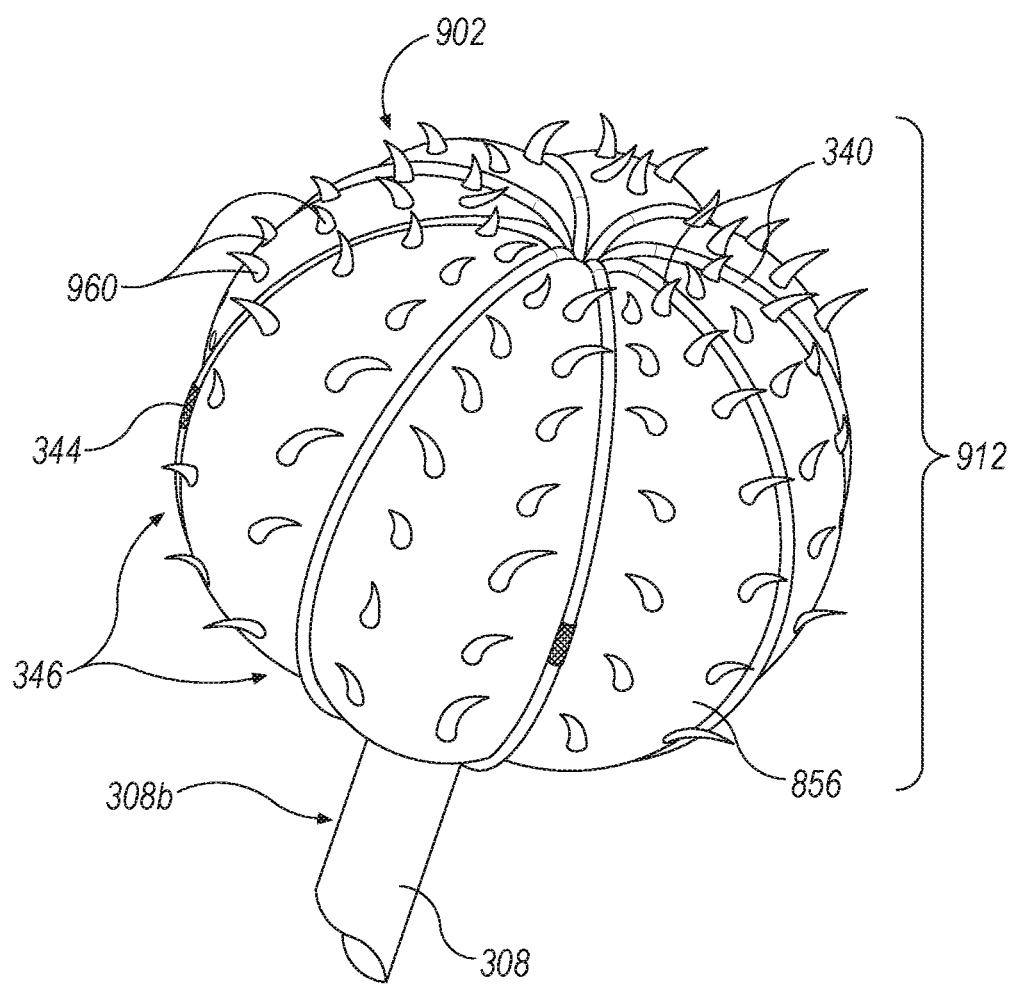
FIG. 9 is an enlarged isometric view of a distal portion of a neuromodulation and mapping device configured in accordance with some embodiments of the present technology.

FIG. 9 is an enlarged isometric view of a distal portion of a neuromodulation and mapping device 902 ("device 902") configured in accordance with some embodiments of the present technology. The device 902 can include various features generally similar to the features of the device 802 described above with reference to FIGS. 8A and 8B. For example, the device 902 includes an evaluation/modulation assembly 912 that includes the plurality of struts 340 (optionally including electrodes 344 disposed thereon) that form the expandable frame or basket 342 and the expandable member 856 (e.g., a balloon) inflatable within the basket 342 via an inflation media (e.g., a fluid, coolant, etc.). As shown in FIG. 9, the expandable member 856 includes one or more protruding or penetrating electrodes 960 that extend across the outer surface of the expandable member 856 in a circumferential pattern to define a three-dimensional microneedle array. The penetrating electrodes 960 can be very small needles and/or other structures with sharp end portions that penetrate a small depth into adjacent tissue when the expandable member 856 is expanded. For example, the needle electrodes 960 may have a tip diameter on the micron level (e.g., 1 micron diameter, 2 micron diameter, 3 micron diameter, 1-20 micron diameter, etc.), a length of 50-350 microns (e.g., 150 microns, 210 microns, 250 microns, etc.), and/or tips coated in platinum black and/or other suitable materials. In other embodiments, the protruding needle electrodes 960 have different sizes, different material composition, and/or are arranged in different patterns across the expandable member 856 (e.g., in an asymmetrical pattern) that facilitate penetration into adjacent tissue and/or detection of desired tissue parameters. In some embodiments, for example, the penetrating electrodes 960 can be fabricated by selective vapor-liquid-solid growth of a silicon wire. In further embodiments, the penetrating electrodes 960 can define a microneedle array on a different portion of the device 902 (e.g., along the struts 340) and/or on a substrate separate from the evaluation/modulation assembly 912. For example, the penetrating electrodes 960 can be positioned on substrate (e.g., a paddle) that can be pressed into contact with tissue to drive the electrodes 960 a small depth into the tissue. The penetrating electrodes 960 may also be deployable and/or retractable. In some embodiments, the penetrating electrodes 960 can be integrated with the metal oxide semiconductor process for high-performance on-chip electronics configurations. In some embodiments, the electrodes 344 on the struts 340 and/or other electrodes on the evaluation/modulation assembly 912 can be replaced by deployable and/or protruding/retractable penetrating needle electrodes.

The electrodes 960 can be used for detection of bioelectric features (e.g., impedance, resistance, etc.) and/or other detectable parameters to allow for mapping of the neural and/or other anatomy at the interest zone before, during, and/or after therapeutic neuromodulation via the other electrodes 344. In other embodiments, the penetrating electrodes 960 can be configured to apply energy for therapeutic neuromodulation. The device 902 requires only a minimal level of invasiveness, but is expected to provide high spatial resolution and high level of accuracy due to the broad area covered by the penetrating electrodes, the high density of the electrodes 960 across the area, and the penetration into the tissue of interest. In some embodiments, for example, the output/input signal amplitude ratios may be >90% at about 40 Hz to about 10 KHz. The device 902 can be used in chronic as well as acute cases.

In various embodiments, the expandable member 856 of the devices 802 and 902 described above with respect to FIGS. 8A-9 can be used as a drug delivery mechanism for delivering a local anesthetic pre- or post-procedurally, a neurotoxin (e.g., to stimulate or modulate nerves at the target site), and/or other drugs or chemicals. The expandable member 856 can be made from a porous material with a plurality of openings or voids for drug expulsion (e.g., eluding drugs disposed within the expandable member 856). The expandable member 856 can also include drugs loaded or embedded within the wall of the expandable member 856 such that pressure against the drug-loaded wall by the tissue causes drug elusion. The neural and anatomical mapping systems and methods described above can be used to ensure precision and accuracy of the drug delivery.

Any of the therapeutic or detection assemblies and devices disclosed herein may be semi-permanently implanted rather than connected to a catheter shaft (for temporary delivery to the treatment site). For implanted embodiments, any of the devices and methods disclosed herein may be used to obtain feedback to locate the appropriate implant site, position the device for long-term implantation, confirm device functionality (e.g., for neural blocking) in-situ and in real-time, and/or to confirm the functionality of the implantable device over the lifetime of the device, the disease, and/or the patient.

In some embodiments, for example, the evaluation/modulation assembly 312 (FIG. 3A) is part of an implantable device separate from the catheter shaft 308 to allow for continued use of the evaluation/modulation assembly 312 over an extended period of time (i.e., not only during the procedure). For example, the implantable device can include a micro-stimulator/modulator (e.g., the evaluation/modulation 312 with the electrodes 344) that is permanently or semi-permanently implanted at a treatment site and a hermetically- or mechanically-sealed controller coupled to the implantable device. In various embodiments, the implantable device can include a variable resistive element, a variable capacitive element, one or more electrodes, and/or fixation or anchoring elements that position the electrodes against tissue within the target site (e.g., within the nasal cavity).

In various embodiments, the implantable device is powered wirelessly by an external unit spaced apart from the monitoring and therapeutic assembly and the treatment site. For example, the external power unit can be worn by the patient, implanted within the patient (e.g., subdermally, within a cavity, etc.) apart from the monitoring and therapeutic assembly, and/or otherwise spaced apart from the treatment site. The device may have a power source that is not reliant on a battery to avoid additional clinical intervention. For example, the device may use capacitive coupling to charge/receive transient charge and/or generation of a magnetic field to couple to the power unit. In some embodiments, magnetic resonant coupling may be the connection mechanism regarding wireless/battery connectivity and coupling.

The implantable device treats conditions, such as rhinitis, by electrically modulating the parasympathetic nerve pathway to the nasal cavity in a similar manner as the system 300 described above with reference to FIGS. 3A-3B, but may provide neural modulation and/or anatomical mapping over an extended period of time (e.g., outside of a procedure) and may be activated at the onset of a predefined sensed trigger (e.g., hyperactivity of the mucosal glad or the parasympathetic nerves). For example, in some embodiments, the modulation may be delivered in bursts in response to threshold levels of autonomic activity. In some embodiments, the modulation may be delivered by a patient in response to symptomatic conditions associated with the disease state (e.g., allergic symptoms as perceived by the patient such as hay fever triggers, sneezing, excessive rhinorrhea, congestion, etc.). The modulation provided by the implantable device may selectively stimulate or modulate parasympathetic fibers, sympathetic fibers, sensory fibers, alpha/beta/delta fibers, C-fibers, anoxic terminals of one or more of the foregoing, insulated over non-insulated fibers (regions with fibers), and/or other neural structures. In some embodiments, the implantable device may selectively target specific cells or cellular regions, such as smooth muscle cells, sub-mucosal glands, goblet cells, stratified cellular regions within the nasal mucosa. These target sites may be identified during anatomical mapping of neural structures and/or other tissues before implantation of the device, during implantation, and/or while the device is implanted.

The implantable device may be deployed at the target site via a delivery system (e.g., a catheter) using anatomical mapping (including neural mapping) for landmarks and positional accuracy as described above. For example, the delivery system may locate and eject the implantable device on, partially within, or fully into the nasal mucosa. The delivery system may be spring loaded, piston activated, hydraulically activated, and/or otherwise activated to deploy the implantable device from a distal end of the delivery system. When the implantable device is configured to be positioned or otherwise anchored at least partially under the surface of the nasal walls, the delivery system may include a suction tip, a needle tip, a dissection tip, a retractable blade with a rotational member/action, and/or other sharp structures that can form an opening and an insertion pathway into the soft tissue.

The implant delivery system may further include linkages or couplings that connect a distal end portion of the delivery system (including deployment and access components) to a proximal handle of the delivery system. Deployment of the implantable device from the delivery system may be driven by sliders, pistons, depression buttons, rotational elements, and/or other actuators at the proximal handle that advance or initiate implantation mechanisms of the delivery system. In some embodiments, the delivery system may have a range/stroke limiting mechanism and/or other restrictive features to limit insertion depth. In some embodiments, the delivery system may have suction functionality to control tissue/device interface and the entry angulation of implant. In some embodiments, the delivery system has an angulated/circumferential orientation control to selectively position implant point of entry. The delivery system may also have micropositional capabilities to fine-tune positional accuracy based on neural locations. In some embodiments, the distal tip of the implantable device is electrically coupled to the delivery system when the implantable device is in a delivery state (before deployment) and acts independently or in conjunction with other features of the delivery system to provide neural mapping and measuring features and refine positional accuracy. In various embodiments, the evaluation/modulation assembly 312 (FIG. 3A) and the device 302 (FIG. 3A) can include similar features as those described above with respect to the implantable device and the delivery system.

The neural and anatomical mapping systems, devices, and methods, disclosed herein can also be used with respect to anatomical structures outside of the nasal cavity and/or additional diseased states, including any peripheral nervous system acute or chronic disease state. The present technology may be used to assess and/or monitor (short-term and/or long-term) neural/neuromuscular degenerative disease states, intraoperative neuroma-in-continuity, and the nerve regeneration and degenerative neuromuscular disorders. Other examples disease states treatable with the present technology include: acute inflammatory demyelinating polyneuropathy ("ADP"), Multiple Sclerosis ("MS"), acute motor axonal neuropathy ("MAN"), Lambert-Eaton myasthenic syndrome ("LEMS"), myasthenia gravis ("MG"), neuromuscular transmission disorders ("NMTD"), peripheral neurophysiological examination ("PNE"), any neuromuscular transmission disorder of nerve terminal function, transmitter production, storage, and/or release, pre-/post-synaptic membrane structure and function, receptor dynamics, endplate potentials, propagated muscle action potentials, and others.

Additional Examples

Several aspects of the present technology are set forth in the following additional examples.

1. A system for detecting anatomical structures and therapeutic neuromodulation in a nasal region of a human patient, the system comprising:
   a shaft having a proximal portion and a distal portion, wherein the shaft is configured to locate the distal portion intraluminally at a target site within a nasal cavity inferior to a sphenopalatine foramen of the human patient;
   an evaluation/modulation assembly at the distal portion of the shaft, wherein the evaluation/modulation assembly comprises a plurality of electrodes configured to emit stimulating energy to tissue at the target site at frequencies for locating target neural structures and detect bioelectric properties in response to the stimulating energy; and
   a console including a controller having a computer-readable medium carrying instructions, which when executed by the controller, causes the console to map locations of the target neural structures and causes the evaluation/modulation assembly to apply therapeutic neuromodulation energy in a predetermined neuromodulation pattern based on the locations of the target neural structures.

2. The system of example 1 wherein at least a portion of the plurality of electrodes are configured to apply RF energy at a predetermined frequency to initiate ionic agitation of the target neural structure to therapeutically modulate postganglionic parasympathetic nerves.

3. The system of example 1 or 2 wherein at least a portion of the plurality of electrodes are configured to apply RF energy at a predetermined frequency to initiate ionic agitation of sub mucosal structures to therapeutically modulate postganglionic parasympathetic tone.

4. The system of any one of examples 1-3 wherein at least a portion of the plurality of electrodes are configured to apply RF energy at a predetermined frequency to initiate vacuolar degeneration of the target neural structure to therapeutically modulate postganglionic parasympathetic nerves.

5. The system of any one of examples 1-4 wherein:
   the plurality of electrodes are configured to detect bioelectric properties of non-target anatomical structures at the target site;
   the computer-readable medium carrying instructions, which when executed by the controller, causes the console to map locations of non-target anatomical structures and causes the evaluation/modulation assembly to apply neuromodulation energy in the predetermined pattern to avoid the locations of the non-target anatomical structures.

6. The system of any one of examples 1-5, further comprising a display configured to visualize locations of the target neural structures with respect to a predicted neuromodulation zone defined by the predetermined neuromodulation pattern.

7. The system of any one of examples 1-6 wherein the plurality of electrodes are configured to detect bioelectric properties of tissue at the treatment site before therapeutic neuromodulation, during therapeutic neuromodulation, and/or after therapeutic neuromodulation.

8. The system of example 7 wherein the bioelectric properties include at least one of complex impedance, resistance, reactance, capacitance, inductance, permittivity, conductivity, nerve firing voltage, nerve firing current, magnetic field, and induced electromotive force.

9. The system of any one of examples 1-8 wherein the evaluation/modulation assembly comprises:
   a basket transformable between a low-profile delivery state and an expanded state, wherein the basket includes plurality of struts spaced radially apart from each other when the basket is in the expanded state, wherein—
   the plurality of electrodes are disposed on the struts,
   the plurality of struts are configured to position at least two of the electrodes at the target site when the basket is in the expanded state, and
   the electrodes are configured to apply radiofrequency (RF) energy to the target site to therapeutically modulate parasympathetic nerves proximate to the target site.

10. The system of example 9 wherein the evaluation/modulation assembly further comprises:
    an expandable member within the basket and transformable between a low-profile delivery state to an expanded state, wherein at least a portion of the plurality of electrodes are disposed on an exterior surface of the expandable surface.

11. The system of example 10 wherein the balloon comprises a plurality of holes configured to allow perfusion of a drug through the balloon when the balloon is in the expanded state.

12. The system of example 9 wherein the evaluation/modulation assembly further comprises:
    an expandable member within the basket and transformable between a low-profile delivery state to an expanded state; and
    at least one sensing electrode disposed on the expandable member, wherein the sensing electrode defines a coiled shape extending around a circumferential portion of the expandable member.

13. The system of example 9 wherein the evaluation/modulation assembly further comprises:
    an expandable member within the basket and transformable between a low-profile delivery state to an expanded state; and
    a plurality of penetrating electrodes disposed on an exterior surface of the expandable member, wherein the expandable member is configured to position at least a portion of the penetrating electrodes a depth into tissue at the target site when the expandable member is in the expanded state.

14. The system of any one of examples 1-13 wherein the plurality of electrodes includes an array of penetrating electrodes configured to penetrate a depth into tissue at the target site when the expandable member is in the expanded state.

15. The system of example 14 wherein the penetrating electrodes are configured to detect muscle contraction in response to the stimulating energy.

16. The system of any one of examples 1-15 wherein the evaluation/modulation assembly comprises a balloon transformable between a low-profile delivery state to an expanded state, wherein at least a portion of the plurality of electrodes are disposed on the balloon.

17. The system of any one of examples 1-16 wherein the plurality of electrodes are configured to be independently activated and independently assigned a selective polarity to apply therapeutic neuromodulation across selected regions of the evaluation/modulation assembly.

18. A system for detecting anatomical structures and therapeutic neuromodulation in a nasal region of a human patient, the system comprising:
    a shaft having a proximal portion and a distal portion, wherein the shaft is configured to locate the distal portion intraluminally at a target site, wherein the target site is at least one of proximate to the sphenopalatine foramen of a human patient or inferior to the sphenopalatine foramen; and
    an evaluation/modulation assembly at the distal portion of the shaft and transformable between a low-profile delivery state and an expanded state, wherein the evaluation/modulation assembly comprises a plurality of electrodes configured to be placed into contact with tissue at the target site when the evaluation/modulation assembly is in the expanded state and measure bioelectric properties of tissue at the target site to identify and locate target anatomical structures and non-target structures; and
    a console including a controller having a computer-readable medium carrying instructions, which when executed by the controller, causes the console to map locations of the target anatomical structures and non-target anatomical structures and causes the evaluation/modulation assembly to apply therapeutic neuromodulation energy in a predetermined neuromodulation pattern based on the locations of the target and non-target anatomical structures.

19. The system of example 18 wherein the instructions, when executed by the controller, causes the evaluation/modulation assembly to determine resistance at least proximate to the target site.

20. The system of example 18 or 19 wherein the bioelectric properties are detected before therapeutic neuromodulation, during therapeutic neuromodulation, and/or after therapeutic neuromodulation, and wherein the bioelectric properties include at least one of complex impedance, resistance, reactance, capacitance, inductance, permittivity, conductivity, nerve firing voltage, nerve firing current, magnetic field, and induced electromotive force.

21. The system of any one of examples 18-20 wherein at least a portion of the plurality of electrodes are configured to apply RF energy at a predetermined frequency to activate target anatomical structures for anatomical mapping and/or therapeutic neuromodulation.

22. The system of examples 18-21 wherein the evaluation/modulation assembly comprises:
    a frame transformable between the low-profile delivery state and the expanded state, wherein the frame includes plurality of struts spaced radially apart from each other when the frame is in the expanded state, and wherein—
    the plurality of electrodes are disposed on the struts, and
    the plurality of struts are configured to position at least two of the electrodes at the target site when the frame is in the expanded state.

23. The system of examples 18-22 wherein the evaluation/modulation assembly comprises an expandable member transformable between the low-profile delivery state to the expanded state, wherein at least a portion of the plurality of electrodes are disposed on the expandable member.

24. A method of therapeutically modulating nerves in a nasal region of a human patient, the method comprising:
  intraluminally advancing an evaluation/modulation assembly at a distal portion of a shaft of a therapeutic device to a target site within the nasal region, wherein the target site is proximate to parasympathetic nerves, and wherein the evaluation/modulation assembly includes a plurality of electrodes;
  delivering stimulation energy to the target site to excite neural structures at the target site, wherein the stimulation energy is emitted at one or more frequencies for locating specific target neural structures;
  detecting one or more bioelectric parameters at the target site via at least a portion of the plurality of electrodes of the evaluation/modulation assembly;
  based on the detected bioelectric parameters, identifying relative presence and position of target neural structures at the target site; and
  determining a neuromodulation pattern based on the locations of the target neural structures to block the detected target neural structures.

25. The method of example 24, further comprising delivering therapeutic neuromodulation energy based on the predetermined neuromodulation pattern.

26. The method of example 25 wherein delivering therapeutic neuromodulation energy further comprises delivering RF energy at a predetermined frequency to initiate ionic agitation of the target neural structure to therapeutically modulate postganglionic parasympathetic nerves.

27. The method of example 25 wherein delivering therapeutic neuromodulation energy further comprises delivering RF energy at a predetermined frequency to initiate ionic agitation of the submucosal structures to therapeutically modulate postganglionic parasympathetic nerves.

28. The method of example 25 wherein delivering therapeutic neuromodulation energy further comprises delivering RF energy at a predetermined frequency to initiate vacuolar degeneration of the target neural structure to therapeutically modulate postganglionic parasympathetic nerves.

29. The method of any one of examples 24-28 wherein detecting one or more bioelectric parameters comprises detecting resistance of the tissue.

30. The method of any one of examples 24-29 wherein detecting one or more bioelectric parameters comprises detecting at least one of nerve firing voltage and nerve firing current.

31. The method of any one of examples 24-30 wherein detecting one or more bioelectric parameters comprises detecting a neuromagnetic field at the target site.

32. The method of any one of examples 24-31 wherein detecting one or more bioelectric parameters comprises detecting induced electromotive force at the target site.

33. The method of any one of examples 24-32 wherein:
  detecting one or more bioelectric parameters at the target site comprises detecting bioelectric parameters of non-target anatomical structures at the target site; and
  the method further comprises identifying locations of non-target structures at the target site based on the detected bioelectric parameters.

34. The method of any one of examples 24-33, further comprising visually mapping locations of the target neural structures with respect to a predicted neuromodulation zone defined by the predetermined neuromodulation pattern.

35. The method of any one of examples 24-34, further comprising, before delivering stimulation energy, deploying an array of penetrating electrodes such that at least a portion of the penetrating electrodes penetrate a depth into the target tissue, the penetrating electrodes being at least a portion of the plurality of electrodes and disposed on the evaluation/modulation assembly.

36. The method of example 35 wherein:
  detecting one or more bioelectric parameters at the target site via at least a portion of the plurality of electrodes of the evaluation/modulation assembly comprises detecting muscle contraction data in response to the stimulation energy via the penetrating electrodes; and
  identifying relative presence and position of target neural structures at the target site comprises mapping locations of target neural structures based on the detected muscle contraction data.

37. A method of therapeutically modulating nerves in a nasal region of a human patient, the method comprising:
  intraluminally advancing an evaluation/modulation assembly at a distal portion of a shaft of a therapeutic device to a target site within the nasal region, wherein the target site is proximate to parasympathetic nerves, and wherein the evaluation/modulation assembly includes a plurality of electrodes;
  before therapeutic neuromodulation, detecting one or more baseline bioelectric parameters at the target site via at least a portion of the plurality of electrodes;
  geometrically identifying inherent tissue properties within the target site based on the detected bioelectric parameters to identify locations of target structures and non-target structures;
  determining a neuromodulation pattern based on the locations of the target structures and the non-target structures; and
  delivering therapeutic neuromodulation energy to the target structures in accordance with the neuromodulation pattern.

38. The method of example 37, further comprising:
  during the delivery of the therapeutic neuromodulation energy, determining one or more mid-procedure bioelectric parameters via the evaluation/modulation assembly; and
  after the delivery of the therapeutic neuromodulation energy, determining one or more post-procedure bioelectric parameters via the evaluation/modulation assembly to determine the effectiveness of the delivery of the therapeutic neuromodulation energy in blocking the nerves that received the therapeutic neuromodulation energy.

39. The method of example 37 or 38 wherein geometrically identifying inherent tissue properties within the target site based on the detected bioelectric parameters comprises detecting nerve firing rate at the target site.

40. The method of any one of examples 37-39 wherein delivering therapeutic neuromodulation energy to the target structures in accordance with the neuromodulation pattern comprises delivering RF energy at a predetermined frequency to initiate ionic agitation of the target structure to therapeutically modulate postganglionic parasympathetic nerves.

41. The method of any one of examples 37-40 wherein delivering therapeutic neuromodulation energy to the target structures in accordance with the neuromodulation pattern comprises delivering RF energy at a predetermined frequency to initiate ionic agitation of submucosal structures to therapeutically modulate postganglionic parasympathetic nerves.

42. The method of any one of examples 37-41 wherein delivering therapeutic neuromodulation energy to the target structures in accordance with the neuromodulation pattern comprises delivering RF energy at a predetermined frequency to initiate vacuolar degeneration of the target structures to therapeutically modulate postganglionic parasympathetic nerves.

43. A device for detecting anatomical structures and therapeutic neuromodulation in a nasal region of a human patient, the system comprising:
  a shaft having a proximal portion and a distal portion, wherein the shaft is configured to locate the distal portion intraluminally at a target site within a nasal cavity inferior to a sphenopalatine foramen of the human patient;
  an evaluation/modulation assembly at the distal portion of the shaft, wherein—
    the evaluation/modulation assembly comprises a plurality of electrodes configured to emit stimulating energy to tissue at the target site at frequencies for locating target structures and non-target structures and detect bioelectric properties in response to the stimulating energy;
    the bioelectric properties are used to map locations of the target structures and the non-target structures; and
    at least a portion of the plurality of electrodes are configured to apply therapeutic neuromodulation energy in a predetermined neuromodulation pattern based on the locations of the target structures and the non-target structures.

44. The device of example 43 wherein at least a portion of the plurality of electrodes are configured to apply RF energy at a predetermined frequency to initiate ionic agitation and/or vacuolar degeneration of the target structures to therapeutically modulate postganglionic parasympathetic nerves.

CONCLUSION

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well-known structures and functions have not been shown and/or described in detail to avoid unnecessarily obscuring the description of the embodiments of the present technology. Although steps of methods may be presented herein in a particular order, in alternative embodiments the steps may have another suitable order. Similarly, certain aspects of the present technology disclosed in the context of particular embodiments can be combined or eliminated in other embodiments. Furthermore, while advantages associated with certain embodiments may have been disclosed in the context of those embodiments, other embodiments can also exhibit such advantages, and not all embodiments need necessarily exhibit such advantages or other advantages disclosed herein to fall within the scope of the present technology. Accordingly, this disclosure and associated technology can encompass other embodiments not expressly shown and/or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the terms "comprising" and the like are used throughout this disclosure to mean including at least the recited feature(s) such that any greater number of the same feature(s) and/or one or more additional types of features are not precluded. Directional terms, such as "upper," "lower," "front," "back," "vertical," and "horizontal," may be used herein to express and clarify the relationship between various elements. It should be understood that such terms do not denote absolute orientation. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

We claim:
1. A treatment system comprising:
  a treatment device comprising a distal assembly comprising a sensing element and an energy delivery element; and
  a console including a controller operably associated with the treatment device, the controller having a computer-readable medium carrying instructions, which, when executed by the controller,
  causes the console to—
    apply signals having a plurality of different frequencies to a treatment site via the energy delivery element of the distal assembly, the different frequencies being configured to differentiate target neural structures from vessels at the treatment site,
    measure responses to the signals having the different frequencies via the sensing element of the distal assembly,
    determine locations and depths of the target neural structures and locations and depths of the vessels at the treatment site based on the measured responses, and
    generate a treatment pattern for the treatment site that targets the locations and depths of the target neural structures and avoids the locations of the vessels at the depths of the vessels, and
  causes the treatment device to apply treatment energy via the energy delivery element of the distal assembly to the treatment site according to the treatment pattern.

2. The system of claim 1 wherein the console is further configured to identify additional anatomical structures based on feedback from the sensing element.

3. The system of claim 1 wherein the console is further configured to confirm efficacy of the treatment and/or enhance performance of the system based on feedback from the sensing element.

4. The system of claim 1 wherein the console is further configured to monitor neural activity and/or temperature at the target neural structures during the treatment based on feedback from the sensing element.

5. The system of claim 4 wherein the console is further configured to automatically shut off the system when the neural activity and/or temperature reaches a predetermined threshold.

6. The system of claim 1 wherein the console comprises a display configured to communicate the measured responses to a user.

7. The system of claim 6 wherein the display is selected from the group consisting of: a monitor, a touchscreen, and a user interface.

8. The system of claim 1 wherein the sensing element comprises one or more electrodes.

9. The system of claim 8 wherein the one or more electrodes provide feedback that comprises one or more resistance values for the target neural structures and the vessels at the treatment site.

10. The system of claim 9 wherein the console further comprises a display configured to communicate the one or more resistance values to a user via a high resolution spatial grid.

11. The system of claim 1 wherein the energy delivery element comprises a cryotherapy treatment element.

12. The system of claim 1 wherein the energy delivery element comprises a delivery state and an expanded state.

13. The system of claim 1 wherein the energy delivery element is configured to deliver radiofrequency energy.

14. The system of claim 13 wherein the energy delivery element comprises a plurality of electrodes.

15. The system of claim 14 wherein the plurality of electrodes is arranged on a plurality of struts.

16. The system of claim 1 wherein the treatment device further comprises a shaft coupled to the distal assembly.

17. The system of claim 16 wherein the treatment device further comprises a handle coupled to the shaft, wherein the handle is configured to allow manipulation of the shaft.

18. The system of claim 16 wherein the shaft is steerable.

19. The system of claim 18 wherein the shaft comprises a bend radius.

20. The system of claim 18 wherein the shaft is steerable in at least two different directions.

21. The system of claim 1 wherein the console is configured to cause the treatment device to apply the treatment energy according to the treatment pattern such that the treatment is provided to the target neural structures and not to the vessels.

22. The system of claim 1 wherein the distal assembly is configured to be inserted into a nasal region of a patient.

* * * * *

UNITED STATES PATENT AND TRADEMARK OFFICE
CERTIFICATE OF CORRECTION

| | |
|---|---|
| PATENT NO. | : 10,806,921 B2 |
| APPLICATION NO. | : 16/696826 |
| DATED | : October 20, 2020 |
| INVENTOR(S) | : Townley et al. |

It is certified that error appears in the above-identified patent and that said Letters Patent is hereby corrected as shown below:

In the Specification

In Column 2, Line 12, delete "chromoglycate," and insert -- cromoglycate, --, therefor.

In Column 9, Line 24, delete "tissue)," and insert -- tissue, --, therefor.

In Column 9, Line 59, delete "1-50Ω" and insert -- 1-50Ω. --, therefor.

In Column 13, Line 60, delete "on an" and insert -- on --, therefor.

In Column 20, Line 50, delete "an a" and insert -- in a --, therefor.

In Column 31, Line 9, delete "of the of the" and insert -- of the --, therefor.

In Column 33, Line 31, delete "for" and insert -- For --, therefor.

In Column 37, Line 63, delete "("ADP")," and insert -- ("AIDP"), --, therefor.

Signed and Sealed this
Seventeenth Day of May, 2022

Katherine Kelly Vidal
*Director of the United States Patent and Trademark Office*